(12) United States Patent
Michaud

(10) Patent No.: US 12,268,839 B2
(45) Date of Patent: *Apr. 8, 2025

(54) DRIVE MECHANISM FOR INFUSION PUMP

(71) Applicant: Tandem Diabetes Care, Inc., San Diego, CA (US)

(72) Inventor: Michael Michaud, San Diego, CA (US)

(73) Assignee: Tandem Diabetes Care, Inc, San Diego, CA (US)

( * ) Notice: Subject to any disclaimer, the term of this patent is extended or adjusted under 35 U.S.C. 154(b) by 649 days.

This patent is subject to a terminal disclaimer.

(21) Appl. No.: 17/478,565

(22) Filed: Sep. 17, 2021

(65) Prior Publication Data

US 2022/0001104 A1    Jan. 6, 2022

Related U.S. Application Data

(63) Continuation of application No. 16/403,016, filed on May 3, 2019, now Pat. No. 11,147,916, which is a (Continued)

(51) Int. Cl.
*A61M 5/142* (2006.01)
*A61M 5/145* (2006.01)

(52) U.S. Cl.
CPC ...... *A61M 5/1452* (2013.01); *A61M 5/14248* (2013.01); *A61M 2005/14268* (2013.01); (Continued)

(58) Field of Classification Search
CPC .............. A61M 5/142; A61M 5/1452; A61M 5/14248; A61M 2205/3306

See application file for complete search history.

(56) References Cited

U.S. PATENT DOCUMENTS 4,019,073 A    4/1977   Vishnevsky et al.
4,741,736 A    5/1988   Brown
(Continued)

FOREIGN PATENT DOCUMENTS

CA    2930776 C    5/2018
CN    1097632 A    1/1995
(Continued)

OTHER PUBLICATIONS

Application and File history for U.S. Appl. No. 15/241,257, filed Aug. 19, 2016. Inventor: Michaud as available on PAIR at www.uspto.gov.

(Continued)

*Primary Examiner* — Laura A Bouchelle
(74) *Attorney, Agent, or Firm* — Merchant & Gould P.C.

(57) ABSTRACT

A patch pump utilizes piezoelectricity to dispense medicament from a cartridge syringe to a patient. Pump can include a plurality of piezoelectric elements that when energized cause linear motion of a pushrod that interfaces with the syringe in the cartridge to advance the syringe and dispense the medicament. The high torque generated by the piezoelectric elements is directly converted into the same amount of torque on the lead screw, so no torque increasing gear reduction system is needed and the pushrod utilized to drive the syringe can be contained within and connected directly to the motor assembly. Such a piezoelectric-based system can therefore be made smaller and with fewer moving parts than an electromagnetic motor of the same capability such that the pump has a smaller size than has heretofore been possible with prior art electromagnetic-based syringe pumps and other pumps that utilize gear reduction systems.

20 Claims, 21 Drawing Sheets

Related U.S. Application Data continuation of application No. 15/241,257, filed on Aug. 19, 2016, now Pat. No. 10,279,107.

(60) Provisional application No. 62/207,748, filed on Aug. 20, 2015.

(52) U.S. Cl.
CPC ............... *A61M 2205/103* (2013.01); *A61M 2205/3306* (2013.01); *A61M 2205/3317* (2013.01)

(56) References Cited

U.S. PATENT DOCUMENTS

| | | | |
|---|---|---|---|
| 5,084,791 A | 1/1992 | Thanos et al. | |
| 5,097,122 A | 3/1992 | Colman et al. | |
| 5,236,416 A | 8/1993 | McDaniel et al. | |
| 5,665,065 A | 9/1997 | Colman et al. | |
| 5,795,327 A | 8/1998 | Wilson et al. | |
| 6,120,460 A | 9/2000 | Abreu | |
| 6,158,431 A | 12/2000 | Poole | |
| 6,295,506 B1 | 9/2001 | Heinonen et al. | |
| 6,362,591 B1* | 3/2002 | Moberg | A61M 5/162 417/18 |
| 6,413,254 B1 | 7/2002 | Hissong et al. | |
| 6,423,035 B1 | 7/2002 | Das et al. | |
| 6,468,242 B1 | 10/2002 | Wilson et al. | |
| 6,485,465 B2 | 11/2002 | Moberg et al. | |
| 6,551,276 B1 | 4/2003 | Mann et al. | |
| 6,554,798 B1 | 4/2003 | Mann et al. | |
| 6,555,986 B2 | 4/2003 | Moberg | |
| 6,641,533 B2 | 11/2003 | Causey, III et al. | |
| 6,659,980 B2 | 12/2003 | Moberg et al. | |
| 6,669,669 B2 | 12/2003 | Flaherty et al. | |
| 6,749,587 B2 | 6/2004 | Flaherty | |
| 6,813,519 B2 | 11/2004 | Lebel et al. | |
| 6,872,200 B2 | 3/2005 | Mann et al. | |
| 6,885,881 B2 | 4/2005 | Leonhardt | |
| 6,913,933 B2 | 7/2005 | Jacobs et al. | |
| 6,918,542 B2 | 7/2005 | Silverbrook et al. | |
| 6,936,029 B2 | 8/2005 | Mann et al. | |
| 6,940,209 B2 | 9/2005 | Henderson | |
| 6,979,326 B2 | 12/2005 | Mann et al. | |
| 6,997,920 B2 | 2/2006 | Mann et al. | |
| 7,064,472 B2 | 6/2006 | Pelrine et al. | |
| 7,066,909 B1 | 6/2006 | Peter et al. | |
| 7,073,713 B2 | 7/2006 | Silverbrook et al. | |
| 7,083,108 B2 | 8/2006 | Silverbrook et al. | |
| 7,092,011 B2 | 8/2006 | Silverbrook et al. | |
| 7,097,104 B2 | 8/2006 | Silverbrook et al. | |
| 7,107,706 B1 | 9/2006 | Bailey, Sr. et al. | |
| 7,109,878 B2 | 9/2006 | Mann et al. | |
| 7,141,812 B2 | 11/2006 | Appleby et al. | |
| 7,144,384 B2 | 12/2006 | Gorman et al. | |
| 7,170,214 B2 | 1/2007 | Henderson et al. | |
| 7,187,404 B2 | 3/2007 | Silverbrook et al. | |
| 7,193,521 B2 | 3/2007 | Moberg et al. | |
| 7,201,319 B2 | 4/2007 | Silverbrook et al. | |
| 7,234,645 B2 | 6/2007 | Silverbrook et al. | |
| 7,256,824 B2 | 8/2007 | Silverbrook | |
| 7,289,142 B2 | 10/2007 | Silverbrook | |
| 7,309,943 B2 | 12/2007 | Henderson et al. | |
| 7,316,700 B2 | 1/2008 | Alden et al. | |
| 7,339,306 B2 | 3/2008 | Henderson | |
| 7,362,971 B2 | 4/2008 | Silverbrook et al. | |
| 7,373,083 B2 | 5/2008 | Silverbrook et al. | |
| 7,377,706 B2 | 5/2008 | Silverbrook et al. | |
| 7,394,182 B2 | 7/2008 | Pelrine et al. | |
| 7,411,204 B2 | 8/2008 | Appleby et al. | |
| 7,460,152 B2 | 12/2008 | Silverbrook et al. | |
| 7,464,580 B2 | 12/2008 | Zeng et al. | |
| 7,475,825 B2 | 1/2009 | Silverbrook et al. | |
| 7,483,050 B2 | 1/2009 | Silverbrook et al. | |
| 7,497,827 B2 | 3/2009 | Brister | |
| 7,517,332 B2 | 4/2009 | Tonelli et al. | |
| 7,524,045 B2 | 4/2009 | Silverbrook et al. | |
| 7,534,226 B2 | 5/2009 | Mernoe et al. | |
| 7,551,202 B2 | 6/2009 | Silverbrook | |
| 7,582,063 B2 | 9/2009 | Wurster et al. | |
| 7,621,893 B2 | 11/2009 | Moberg et al. | |
| 7,654,127 B2 | 2/2010 | Krulevitch et al. | |
| 7,704,227 B2 | 4/2010 | Moberg et al. | |
| 7,708,717 B2 | 5/2010 | Estes et al. | |
| 7,713,574 B2 | 5/2010 | Brister et al. | |
| 7,714,889 B2 | 5/2010 | Silverbrook | |
| 7,736,344 B2 | 6/2010 | Moberg et al. | |
| 7,744,589 B2 | 6/2010 | Mounce et al. | |
| 7,766,873 B2 | 8/2010 | Moberg et al. | |
| 7,774,145 B2 | 8/2010 | Brauker et al. | |
| 7,776,030 B2 | 8/2010 | Estes et al. | |
| 7,782,192 B2 | 8/2010 | Jeckelmann et al. | |
| 7,786,648 B2 | 8/2010 | Xu et al. | |
| 7,794,427 B2 | 9/2010 | Estes et al. | |
| 7,794,428 B2 | 9/2010 | Estes et al. | |
| 7,806,868 B2 | 10/2010 | De Polo et al. | |
| 7,819,843 B2 | 10/2010 | Mann et al. | |
| 7,887,512 B2 | 2/2011 | Estes et al. | |
| 7,892,206 B2 | 2/2011 | Moberg et al. | |
| 7,905,868 B2 | 3/2011 | Moberg et al. | |
| 7,935,104 B2 | 5/2011 | Yodfat et al. | |
| 7,938,803 B2 | 5/2011 | Mernoe et al. | |
| 7,944,366 B2 | 5/2011 | Krulevitch et al. | |
| 7,955,295 B2 | 6/2011 | Lee et al. | |
| 7,963,945 B2 | 6/2011 | Miller et al. | |
| 7,981,084 B2 | 7/2011 | Estes et al. | |
| 7,988,660 B2 | 8/2011 | Byland et al. | |
| 7,993,109 B2 | 8/2011 | Rush et al. | |
| 7,998,110 B2 | 8/2011 | Leung et al. | |
| 7,998,111 B2 | 8/2011 | Moberg et al. | |
| 7,999,674 B2 | 8/2011 | Kamen | |
| 8,062,257 B2 | 11/2011 | Moberg et al. | |
| 8,065,096 B2 | 11/2011 | Moberg et al. | |
| 8,095,123 B2 | 1/2012 | Gray | |
| 8,100,852 B2 | 1/2012 | Moberg et al. | |
| 8,105,279 B2 | 1/2012 | Mernoe et al. | |
| 8,117,481 B2 | 2/2012 | Anselmi et al. | |
| 8,126,728 B2 | 2/2012 | Dicks et al. | |
| 8,182,447 B2 | 5/2012 | Moberg et al. | |
| 8,187,228 B2 | 5/2012 | Bikovsky | |
| 8,217,533 B2 | 7/2012 | Jones et al. | |
| 8,267,893 B2 | 9/2012 | Moberg et al. | |
| 8,282,601 B2 | 10/2012 | Mernoe et al. | |
| 8,285,328 B2 | 10/2012 | Caffey et al. | |
| 8,287,495 B2 | 10/2012 | Michaud et al. | |
| 8,298,184 B2 | 10/2012 | Diperna et al. | |
| 8,299,733 B2 | 10/2012 | Sattler et al. | |
| 8,304,960 B2 | 11/2012 | Sattler et al. | |
| 8,323,188 B2 | 12/2012 | Tran | |
| 8,343,092 B2 | 1/2013 | Rush et al. | |
| 8,382,703 B1 | 2/2013 | Abdelaal | |
| 8,408,421 B2 | 4/2013 | Diperna | |
| 8,414,563 B2 | 4/2013 | Kamen et al. | |
| 8,444,595 B2 | 5/2013 | Brukalo et al. | |
| 8,448,824 B2 | 5/2013 | Diperna | |
| 8,449,523 B2 | 5/2013 | Brukalo et al. | |
| 8,450,905 B2 | 5/2013 | Guidarelli et al. | |
| 8,451,230 B2 | 5/2013 | Celentano et al. | |
| 8,452,953 B2 | 5/2013 | Buck et al. | |
| 8,466,637 B2 | 6/2013 | Guidarelli et al. | |
| 8,502,662 B2 | 8/2013 | Pohlman et al. | |
| 8,517,991 B2 | 8/2013 | Clemente | |
| 8,562,590 B2 | 10/2013 | Yodfat et al. | |
| 8,573,027 B2 | 11/2013 | Rosinko et al. | |
| 8,601,465 B2 | 12/2013 | Bernstein et al. | |
| 8,641,671 B2 | 2/2014 | Michaud et al. | |
| 8,650,937 B2 | 2/2014 | Brown | |
| 8,758,323 B2 | 6/2014 | Michaud et al. | |
| 8,926,561 B2 | 1/2015 | Verhoef et al. | |
| 8,986,253 B2 | 3/2015 | Diperna | |
| 8,986,523 B2 | 3/2015 | Ackerson et al. | |
| 9,173,998 B2 | 11/2015 | Rosinko et al. | |
| 9,180,242 B2 | 11/2015 | Metzmaker et al. | |
| 9,180,243 B2 | 11/2015 | Michaud | |

(56) References Cited

U.S. PATENT DOCUMENTS

| | | |
|---|---|---|
| 9,211,377 B2 | 12/2015 | Diperna et al. |
| 9,238,100 B2 | 1/2016 | Kruse et al. |
| 9,242,043 B2 | 1/2016 | Ludolph |
| 9,335,910 B2 | 5/2016 | Farnan et al. |
| 9,362,851 B2 | 6/2016 | Xu et al. |
| 9,421,329 B2 | 8/2016 | Kruse |
| 9,555,186 B2 | 1/2017 | Kruse |
| 9,675,756 B2 | 6/2017 | Kamen |
| 9,962,486 B2 | 5/2018 | Rosinko et al. |
| 9,993,595 B2 | 6/2018 | Michaud et al. |
| 10,010,674 B2 | 7/2018 | Rosinko et al. |
| 10,279,106 B1 | 5/2019 | Cook et al. |
| 10,279,107 B2 * | 5/2019 | Michaud ............. A61M 5/1452 |
| 10,357,603 B2 | 7/2019 | Michaud et al. |
| 10,850,032 B2 | 12/2020 | Steck et al. |
| 11,147,916 B2 * | 10/2021 | Michaud ........... A61M 5/14248 |
| 2003/0060768 A1 | 3/2003 | Kiyatake et al. |
| 2004/0204673 A1 | 10/2004 | Flaherty |
| 2004/0220551 A1 | 11/2004 | Flaherty et al. |
| 2005/0177111 A1 | 8/2005 | Ozeri et al. |
| 2006/0049720 A1 | 3/2006 | Henderson et al. |
| 2007/0093753 A1 | 4/2007 | Krulevitch et al. |
| 2007/0149926 A1 | 6/2007 | Moberg et al. |
| 2007/0156092 A1 | 7/2007 | Estes et al. |
| 2007/0167905 A1 | 7/2007 | Estes et al. |
| 2007/0173762 A1 | 7/2007 | Estes et al. |
| 2007/0270750 A1 | 11/2007 | Dacquay |
| 2008/0045902 A1 | 2/2008 | Estes et al. |
| 2008/0045903 A1 | 2/2008 | Estes et al. |
| 2008/0045904 A1 | 2/2008 | Estes et al. |
| 2008/0045931 A1 | 2/2008 | Estes et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051711 A1 | 2/2008 | Mounce et al. |
| 2008/0051716 A1 | 2/2008 | Stutz |
| 2008/0051727 A1 | 2/2008 | Moberg et al. |
| 2008/0097291 A1 | 4/2008 | Hanson et al. |
| 2008/0097375 A1 | 4/2008 | Bikovsky |
| 2008/0097381 A1 | 4/2008 | Moberg et al. |
| 2008/0125700 A1 | 5/2008 | Moberg et al. |
| 2008/0215035 A1 | 9/2008 | Yodfat et al. |
| 2008/0221523 A1 | 9/2008 | Moberg et al. |
| 2009/0036870 A1 | 2/2009 | Mounce et al. |
| 2009/0124994 A1 | 5/2009 | Roe |
| 2009/0157003 A1 | 6/2009 | Jones |
| 2009/0192724 A1 | 7/2009 | Brauker et al. |
| 2009/0270811 A1 | 10/2009 | Mounce et al. |
| 2009/0287180 A1 | 11/2009 | Diperna |
| 2010/0037680 A1 | 2/2010 | Moberg et al. |
| 2010/0078017 A1 | 4/2010 | Andrieux et al. |
| 2010/0121169 A1 | 5/2010 | Petisce et al. |
| 2010/0152674 A1 | 6/2010 | Kavazov et al. |
| 2010/0179402 A1 | 7/2010 | Goode et al. |
| 2010/0185142 A1 | 7/2010 | Kamen et al. |
| 2010/0185175 A1 | 7/2010 | Kamen et al. |
| 2010/0198183 A1 | 8/2010 | Lanigan et al. |
| 2010/0211003 A1 | 8/2010 | Sundar |
| 2010/0217192 A1 | 8/2010 | Moberg et al. |
| 2010/0217193 A1 | 8/2010 | Moberg et al. |
| 2010/0249706 A1 | 9/2010 | Clemente |
| 2010/0324398 A1 | 12/2010 | Tzyy-Ping |
| 2011/0054390 A1 | 3/2011 | Searle et al. |
| 2011/0092948 A1 | 4/2011 | Shachar et al. |
| 2011/0144586 A1 | 6/2011 | Michaud et al. |
| 2011/0144616 A1 | 6/2011 | Michaud et al. |
| 2011/0152770 A1 | 6/2011 | Diperna et al. |
| 2011/0152824 A1 | 6/2011 | Diperna et al. |
| 2011/0152827 A1 | 6/2011 | Wiegel et al. |
| 2011/0160654 A1 | 6/2011 | Hanson et al. |
| 2011/0166544 A1 | 7/2011 | Verhoef et al. |
| 2011/0190614 A1 | 8/2011 | Brister et al. |
| 2011/0190694 A1 | 8/2011 | Lanier, Jr. et al. |
| 2011/0213329 A1 | 9/2011 | Yodfat et al. |
| 2011/0257895 A1 | 10/2011 | Brauker et al. |
| 2012/0029433 A1 | 2/2012 | Michaud et al. |
| 2012/0029468 A1 | 2/2012 | Diperna |
| 2012/0030610 A1 | 2/2012 | Diperna et al. |
| 2012/0041387 A1 | 2/2012 | Bruggermann et al. |
| 2012/0078181 A1 | 3/2012 | Smith et al. |
| 2012/0096954 A1 | 4/2012 | Vazquez et al. |
| 2012/0123230 A1 | 5/2012 | Brown et al. |
| 2012/0172817 A1 | 7/2012 | Brueggemann et al. |
| 2012/0259282 A1 | 10/2012 | Alderete, Jr |
| 2013/0053816 A1 | 2/2013 | Diperna et al. |
| 2013/0150766 A1 | 6/2013 | Olde |
| 2013/0159456 A1 | 6/2013 | Daoud et al. |
| 2013/0204542 A1 | 8/2013 | Olde |
| 2013/0324928 A1 | 12/2013 | Kruse |
| 2013/0331790 A1 | 12/2013 | Brown et al. |
| 2013/0332874 A1 | 12/2013 | Rosinko et al. |
| 2014/0039392 A1 | 2/2014 | Geipel et al. |
| 2014/0039396 A1 | 2/2014 | Geipel et al. |
| 2014/0054883 A1 | 2/2014 | Lanigan et al. |
| 2014/0273042 A1 | 9/2014 | Saint |
| 2014/0276419 A1 | 9/2014 | Rosinko et al. |
| 2014/0276420 A1 | 9/2014 | Rosinko |
| 2014/0276423 A1 | 9/2014 | Lecanu-Fayet |
| 2014/0276531 A1 | 9/2014 | Walsh |
| 2014/0276537 A1 | 9/2014 | Kruse |
| 2014/0276553 A1 | 9/2014 | Rosinko et al. |
| 2014/0276556 A1 | 9/2014 | Saint et al. |
| 2014/0276569 A1 | 9/2014 | Kruse |
| 2014/0276570 A1 | 9/2014 | Saint |
| 2014/0276574 A1 | 9/2014 | Saint |
| 2014/0378898 A1 | 12/2014 | Rosinko |
| 2015/0072613 A1 | 3/2015 | Swanson |
| 2015/0073337 A1 | 3/2015 | Saint et al. |
| 2015/0174320 A1 | 6/2015 | Grant |
| 2015/0182693 A1 | 7/2015 | Rosinko |
| 2015/0182694 A1 | 7/2015 | Rosinko |
| 2015/0182695 A1 | 7/2015 | Rosinko |
| 2015/0202375 A1 | 7/2015 | Schabbach et al. |
| 2016/0030669 A1 | 2/2016 | Harris et al. |
| 2016/0051758 A1 | 2/2016 | Rosinko et al. |
| 2016/0082186 A1 | 3/2016 | Rosinko et al. |
| 2016/0082188 A1 | 3/2016 | Blomquist et al. |
| 2016/0136357 A1 | 5/2016 | Yang |
| 2016/0157759 A1 | 6/2016 | Yang |
| 2016/0157765 A1 | 6/2016 | Zhu |
| 2016/0158436 A1 | 6/2016 | Yang |
| 2016/0199572 A1 | 7/2016 | Yang |
| 2016/0339172 A1 | 11/2016 | Michaud et al. |
| 2017/0049957 A1 | 2/2017 | Michaud |
| 2017/0056581 A1 | 3/2017 | Deak et al. |
| 2018/0071454 A1 | 3/2018 | Betts et al. |
| 2018/0264189 A1 | 9/2018 | Michaud et al. |
| 2019/0240398 A1 | 8/2019 | Seitz et al. |
| 2019/0321546 A1 | 10/2019 | Michaud et al. |

FOREIGN PATENT DOCUMENTS

| | | |
|---|---|---|
| CN | 1611001 A | 4/2005 |
| CN | 101563120 A | 10/2009 |
| CN | 101574550 A | 11/2009 |
| CN | 102378656 A | 3/2012 |
| CN | 101745163 B | 12/2013 |
| CN | 104203315 A | 12/2014 |
| EP | 2420274 A1 | 2/2012 |
| EP | 2510960 A1 | 10/2012 |
| JP | H11267202 A | 10/1999 |
| WO | 0228532 A2 | 4/2002 |
| WO | 0228532 A9 | 5/2003 |
| WO | 2008024808 A2 | 2/2008 |
| WO | 2008024812 A2 | 2/2008 |
| WO | 2009013736 A1 | 1/2009 |
| WO | 2009016636 A2 | 2/2009 |
| WO | 2010096449 A2 | 8/2010 |

(56) References Cited

OTHER PUBLICATIONS

Application and File history for U.S. Appl. No. 16/266,471, filed Feb. 4, 2019. Inventors: Seitz et al., as available on PAIR at www.USPTO.gov.
Communication dated Feb. 17, 2020 for EP Application 16837895.8, 5 pages.
Extended European Search Report in EP16837895.8, mailed Nov. 7, 2018, 8 pages.
International Preliminary Report on Patentability in PCT/US2016/047725, mailed Mar. 1, 2018, 8 pages.
International Search Report and Written Opinion in PCT/US2016/047725, mailed Nov. 28, 2016, 12 pages.
International Search Report and Written Opinion in PCT/US2019/016466, mailed May 22, 2019, 13 pages.
Office Action in CN201680061057.X, dated Dec. 11, 2019, 17 pages.
Search Report in CN202011040886, dated Jul. 11, 2023.

\* cited by examiner

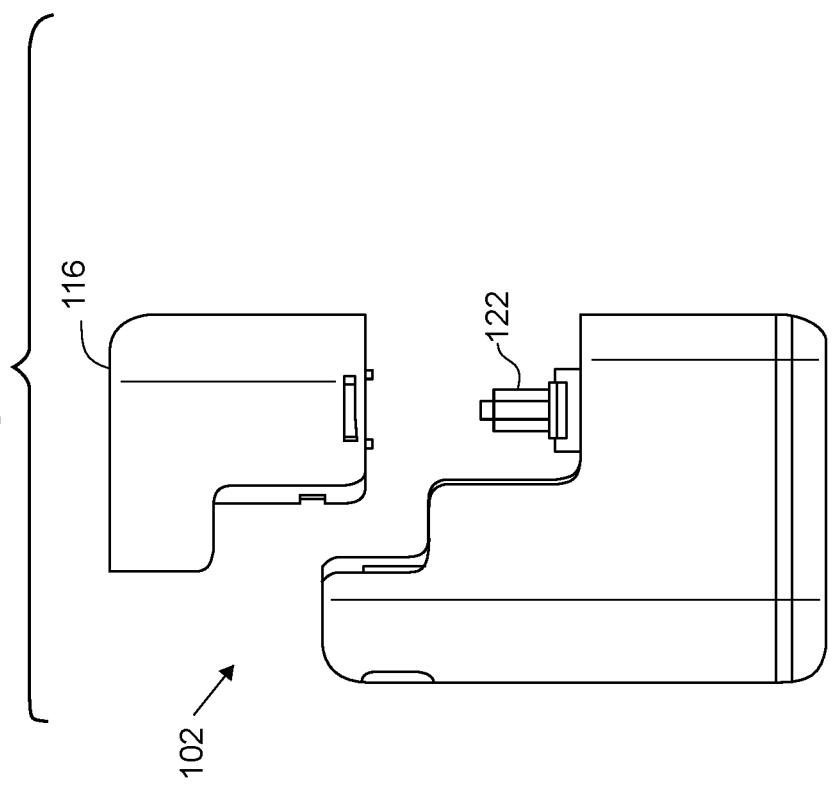
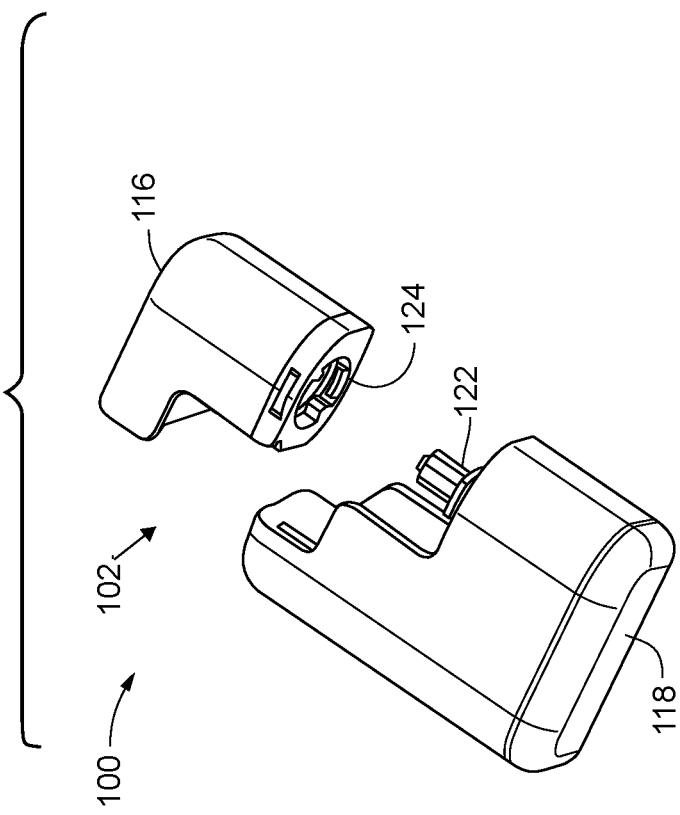

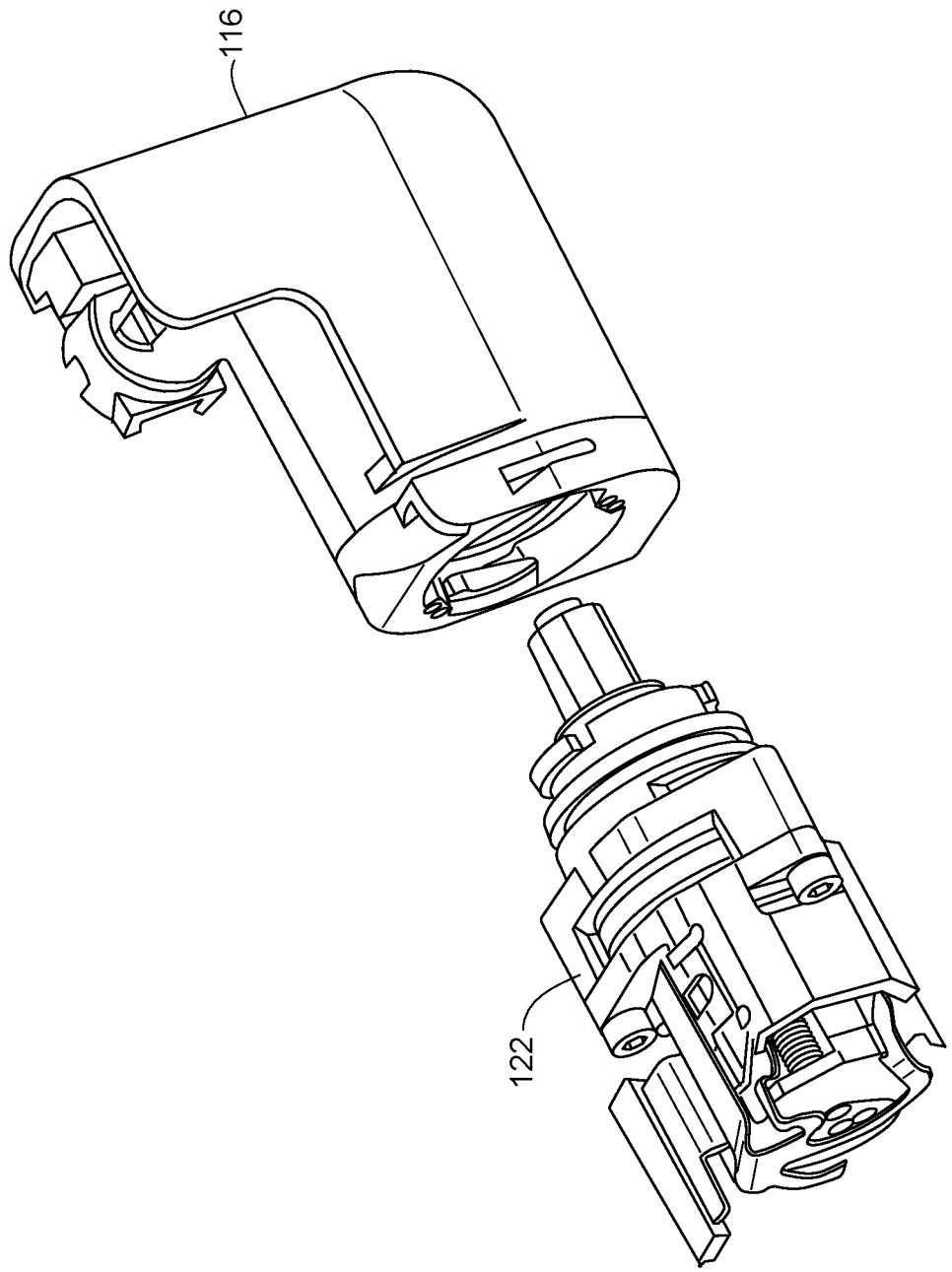

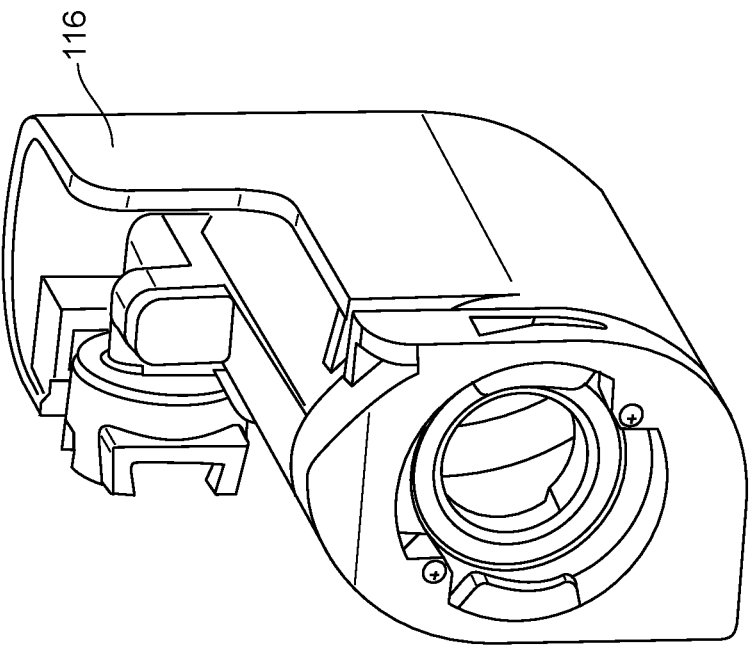
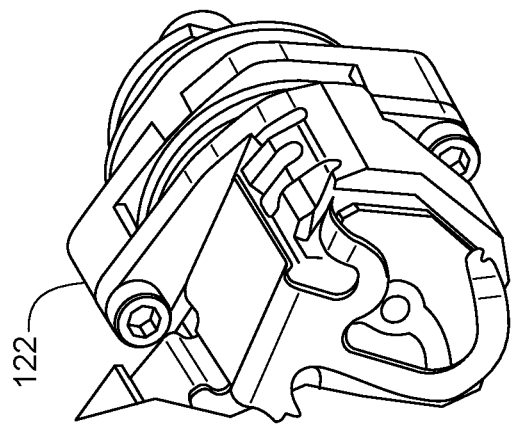
Fig. 3B

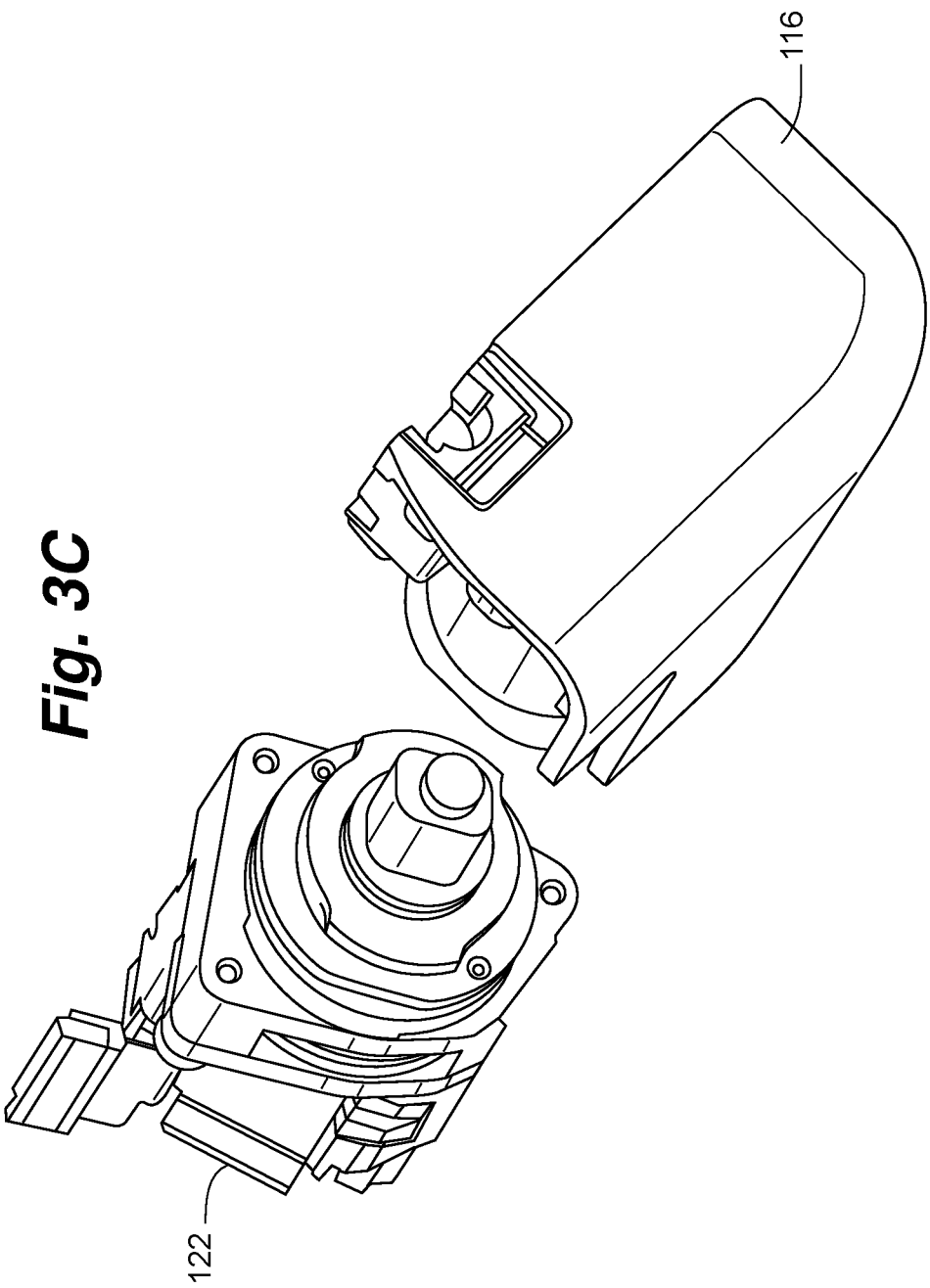

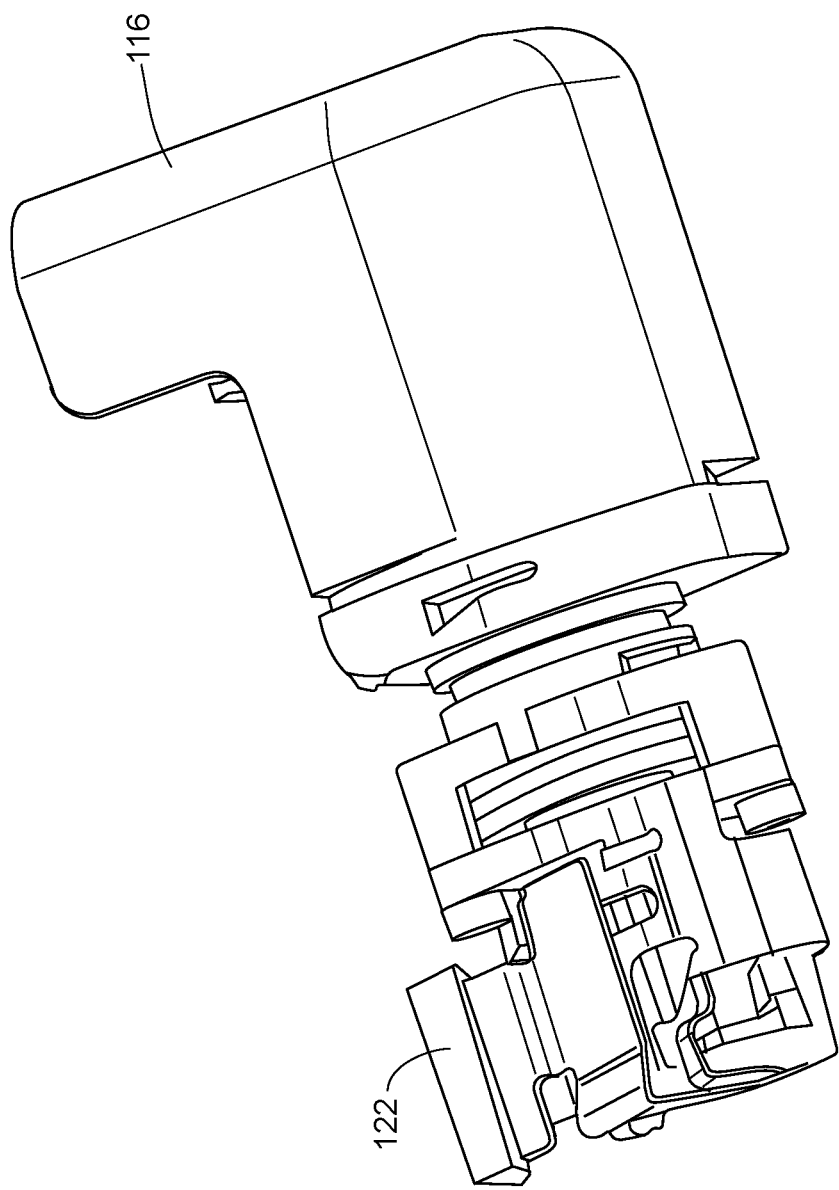

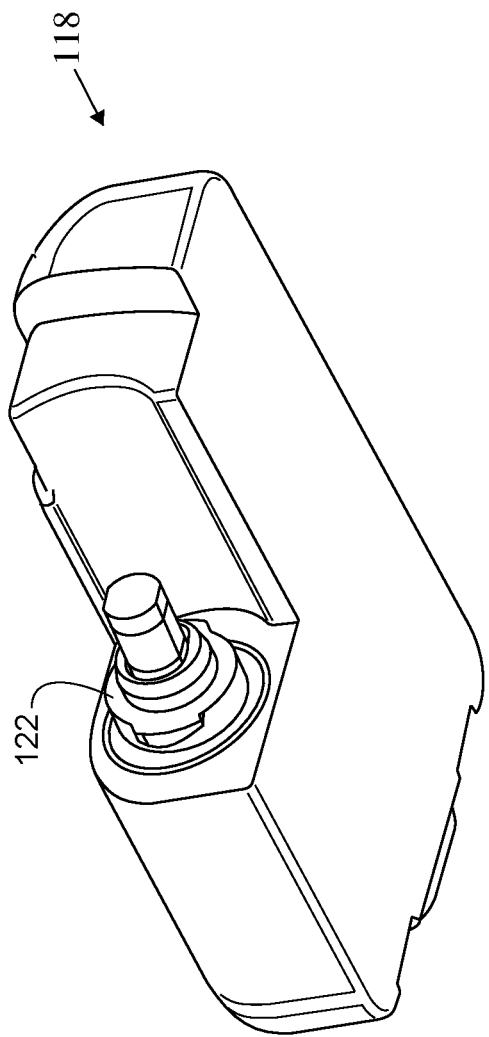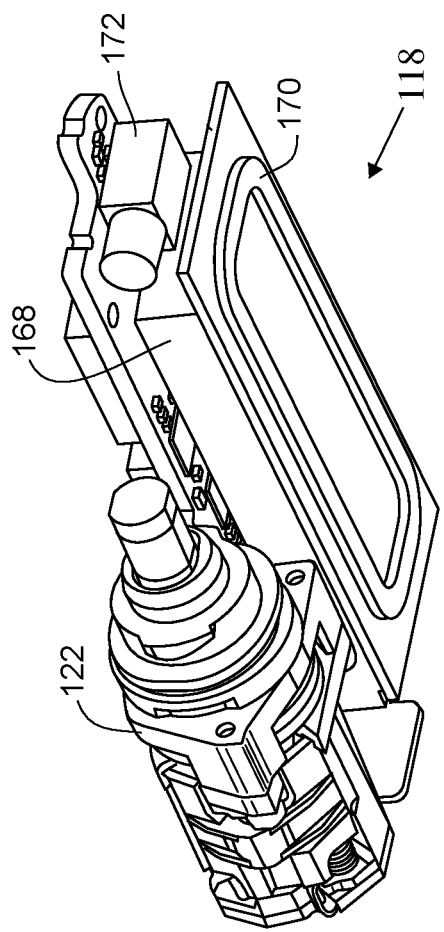

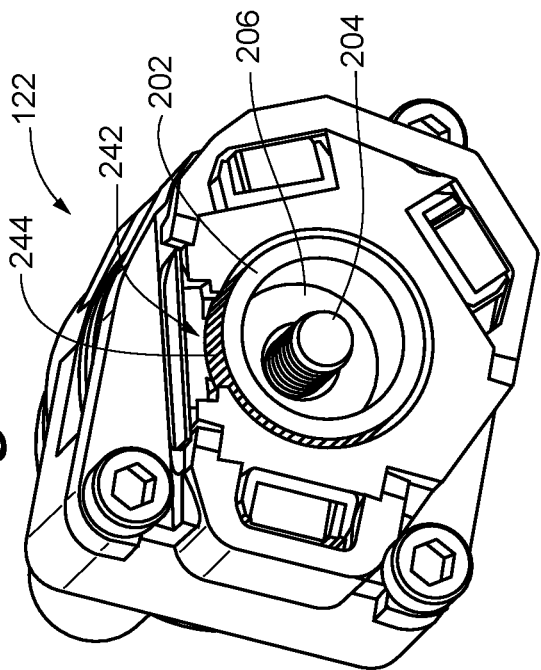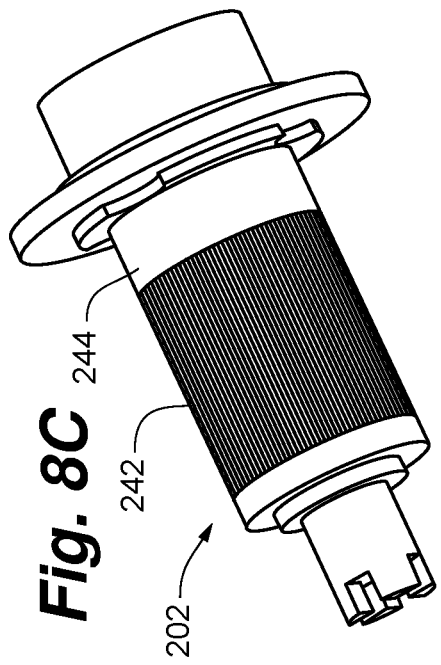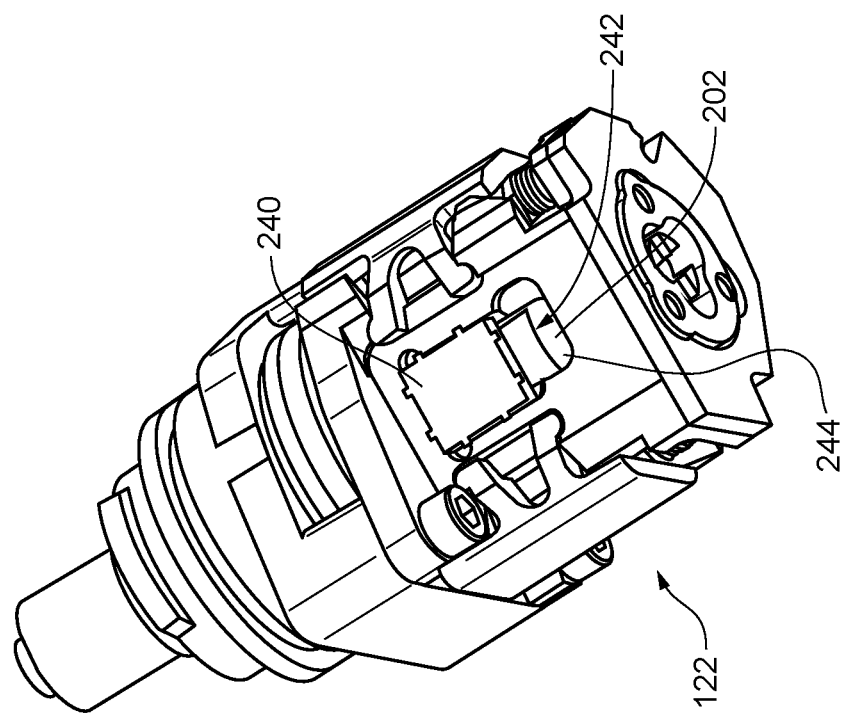

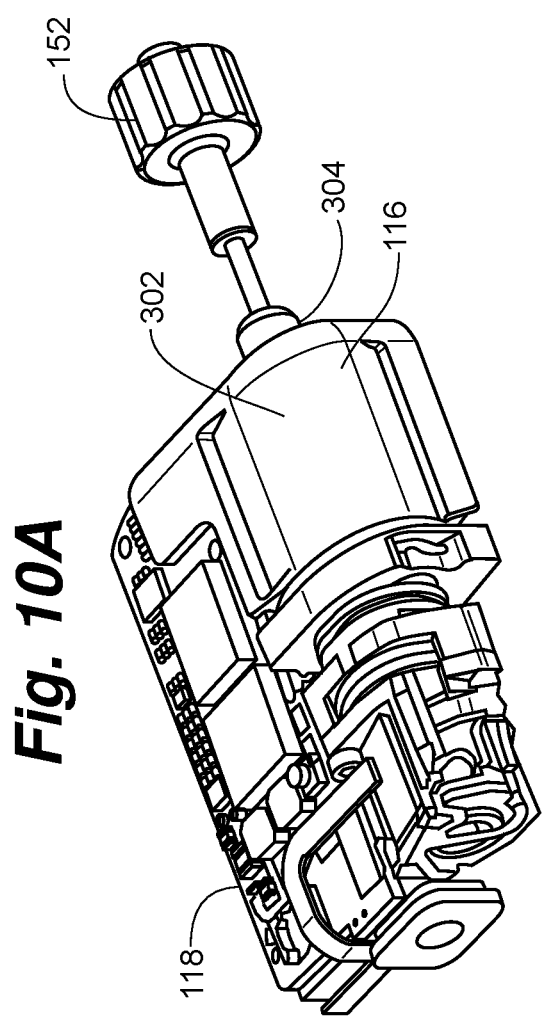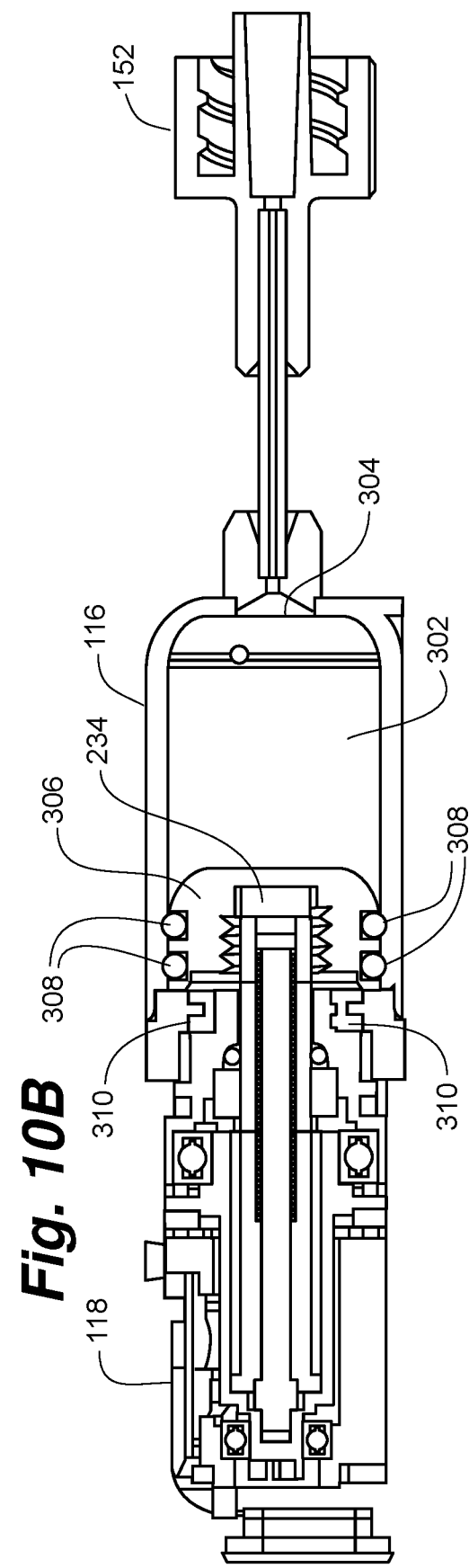

DRIVE MECHANISM FOR INFUSION PUMP

RELATED APPLICATIONS

This application is a continuation of U.S. patent application Ser. No. 16/403,016 filed May 3, 2019, which is a continuation of U.S. patent application Ser. No. 15/241,257 filed Aug. 19, 2016, now U.S. Pat. No. 10,279,107 which claims the benefit of U.S. Provisional Application No. 62/207,748 filed Aug. 20, 2015, each of which is hereby incorporated herein in its entirety by reference.

FIELD OF THE INVENTION

The present invention relates to medical pumps for delivering medicament to a patient and, more specifically, to a drive mechanism for a user-wearable pump, such as a patch pump, for delivering medicament such as insulin to a patient.

BACKGROUND OF THE INVENTION

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

One category of devices for delivering such fluids is that of pumps that have been developed for the administration of insulin and other medicaments for those suffering from both type I and type II diabetes. Some pumps configured as portable infusion devices can provide continuous subcutaneous medicament injection and/or infusion therapy for the treatment of diabetes. Such therapy may include, e.g., the regular and/or continuous injection or infusion of insulin into a person suffering from diabetes and offer an alternative to multiple daily injections of insulin by an insulin syringe or an insulin pen. Such pumps can be ambulatory/portable infusion pumps that are worn by the user and may use replaceable cartridges. Such pumps can deliver medicaments other than or in addition to insulin, such as glucagon. Examples of such pumps and various features that can be associated with such pumps include those disclosed in U.S. Patent Application Publication No. 2013/0053816, U.S. Pat. Nos. 8,573,027, 8,986,253, U.S. Patent Application Publication No. 2013/0324928, U.S. Patent Application Publication No. 2013/0331790 and U.S. Pat. No. 8,287,495, each of which is hereby incorporated herein by reference in its entirety.

One type of pump that has been developed is a patch pump, or micro pump. Patch pumps generally are small pumps, typically ambulatory, that are carried directly on the skin under the user's clothing. Many such pumps are situated directly on the infusion site such that no tubing is required to deliver the insulin and/or other medicament to the patient. Other patch pumps can be positioned on the patient's body with a short length of tubing extending to a nearby infusion site. Not unlike other types of pumps, but perhaps more typically, patch pumps can be at least in part disposable, meant to be worn for a period of time such as, e.g., a day or two, and then discarded and replaced by a new patch pump. Other patch pump designs contemplate a disposable component, such as a cartridge that contains medicament, and a reusable or durable component. In such configurations, the disposable and durable components may be joined together by the patient or caregiver in preparation for delivery of the medicament.

SUMMARY

A patch pump utilizes piezoelectricity to dispense medicament from a cartridge syringe to a patient. Pump can include a plurality of piezoelectric elements that when energized cause linear motion of a pushrod that interfaces with the syringe in the cartridge to advance the syringe and dispense the medicament. The high torque generated by the piezoelectric elements is directly converted into the same amount of torque on the lead screw, so no torque increasing gear reduction system is needed and the pushrod utilized to drive the syringe can be contained within and connected directly to the motor assembly. Such a piezoelectric-based system can therefore be made smaller and with fewer moving parts than an electromagnetic motor of the same capability such that the pump has a smaller size than has heretofore been possible with prior art electromagnetic-based syringe pumps and other pumps that utilize gear reduction systems.

In some embodiments, a user-wearable infusion pump includes a disposable cartridge and a drive unit. The disposable cartridge can include a reservoir configured to contain a medicament, a plunger at a proximal end of the reservoir and an outlet port in fluid communication with the reservoir. The drive unit can include at least one piezoelectric motor and a pushrod and be configured such that when the piezoelectric motor is energized with an electrical drive signal, it causes linear motion of the pushrod that moves the plunger to cause medicament to flow from the reservoir out of the outlet port to a patient without a gear reduction system.

In some embodiments, a user-wearable infusion pump includes a disposable cartridge and a drive unit. The disposable cartridge can include a reservoir configured to contain a medicament, a plunger at a proximal end of the reservoir and an outlet port in fluid communication with the reservoir. The drive unit can include a drive disk having a body defining a central opening through which a drive tube extends such that rotation of the drive disk caused by a motor causes rotation of the drive tube. An externally threaded lead screw can be coupled to the drive tube such that rotation of the drive tube causes rotation of the lead screw. A pushrod having a distal tip can have internal threads configured to mate with the externally threaded lead screw and a guide bushing can surround a portion of the pushrod to prevent rotation of the pushrod such that rotation of the drive screw causes linear motion of the pushrod. Thus, when the motor is actuated to rotate the drive disk, the pushrod is linearly advanced such that the distal tip contacts the plunger in the cartridge and moves the plunger to dispense medicament from the reservoir out the outlet port.

In some embodiments, a user-wearable infusion pump, includes a reservoir configured to contain a medicament, an outlet port in fluid communication with the reservoir, at least one piezoelectric motor and a pushrod. When the at least one piezoelectric motor is energized with an electrical drive signal, it causes linear motion of the pushrod without a gear reduction system that causes medicament to flow from the reservoir out of the outlet port to a patient.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 1A-1E are views of portions of a patch pump system according to embodiments of the present invention.

FIGS. 3A-3D are schematic representations of a cartridge and drive mechanism of a patch pump system according to an embodiment of the present invention.

FIGS. 4A-4C depict various views of a drive unit for a patch pump according to an embodiment of the present invention.

FIGS. 5A-5C depict various views of the drive unit of FIGS. 4A-4C with the housing removed.

FIGS. 8A-8C depict various views of a drive mechanism for a patch pump according to an embodiment of the present invention.

FIGS. 10A-10C depict a medicament cartridge for a patch pump according to an embodiment of the present invention.

Figure 1C:
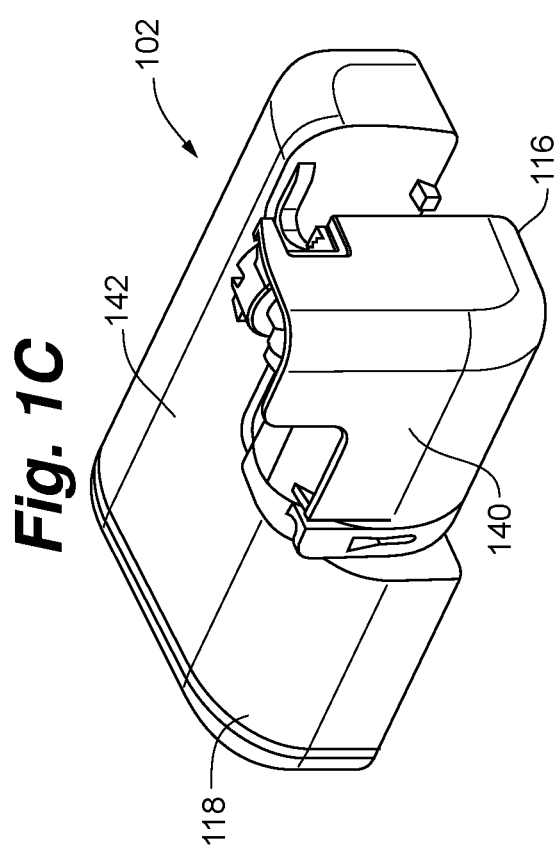

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

FIGS. 1A-1E depict a patch pump system 100 including a pump 102 according to an embodiment of the invention. Drive unit 118 of pump 102 includes a drive mechanism 122 that mates with a recess 124 in disposable cartridge 116 of pump 102 to attach the cartridge 116 to the drive unit 118 and provide for delivery of medicament such as insulin from the cartridge 116 to a user through a cannula. A patch pump system 100 according to embodiments of the present invention can include a pump 102 including a drive unit 118 and a cartridge 116 as well as any additional components, such as for example, an infusion set, some of which will be described herein. Further details regarding such patch pumps can be found in U.S. patent application Ser. No. 14/707,851 filed May 8, 2015 and U.S. patent application Ser. No. 15/158,125 filed May 18, 2016, which are hereby incorporated herein by reference in their entireties.

Figure 1E:
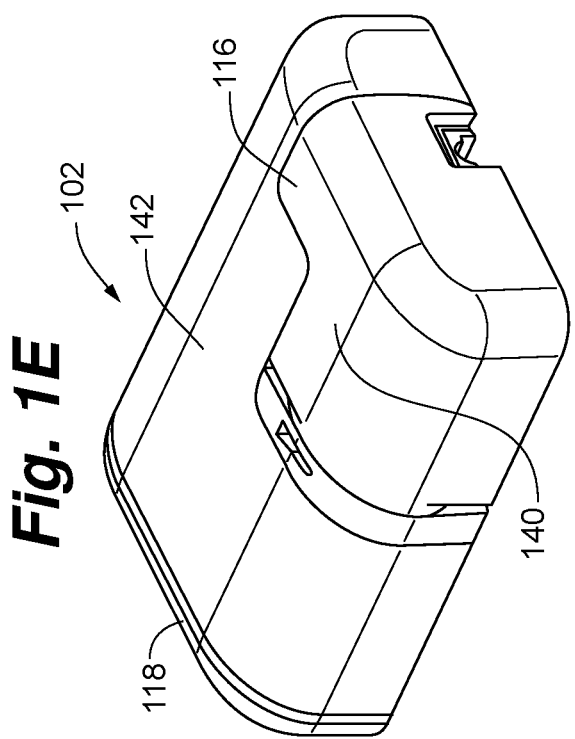
Figure 1D:
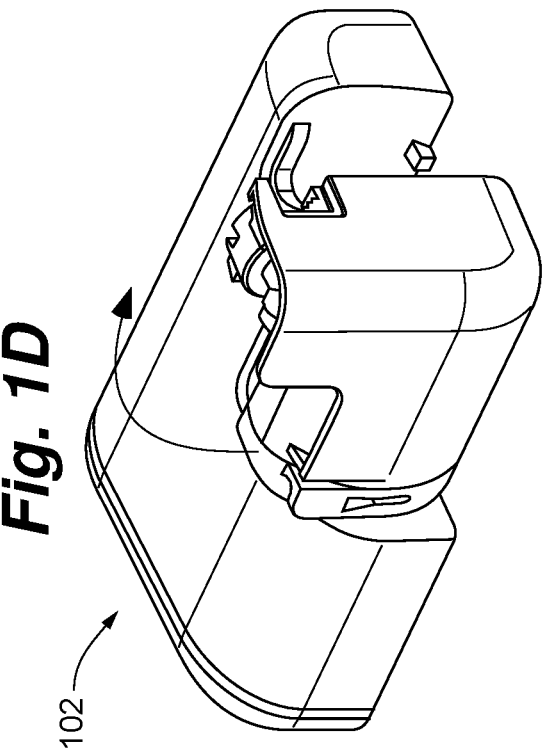
Figure 2A:
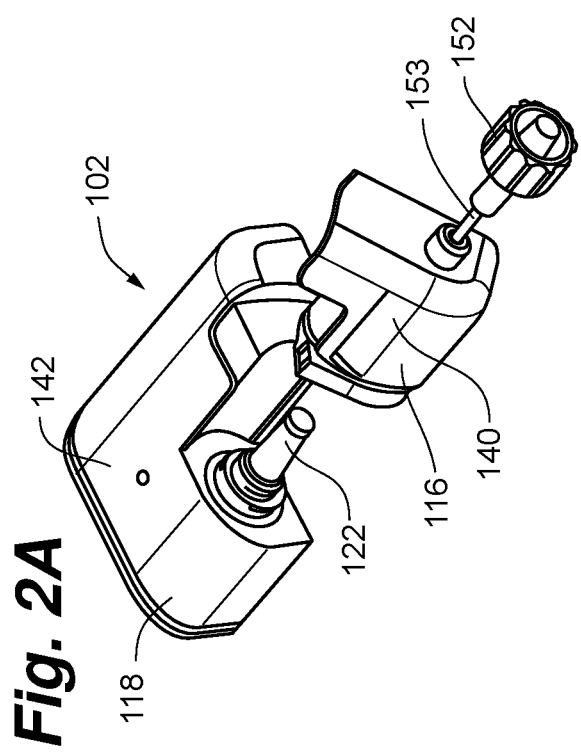
FIGS. 2A-2C depict a cartridge being attached to a drive unit of a patch pump system according to an embodiment of the present invention.
Figure 2B:
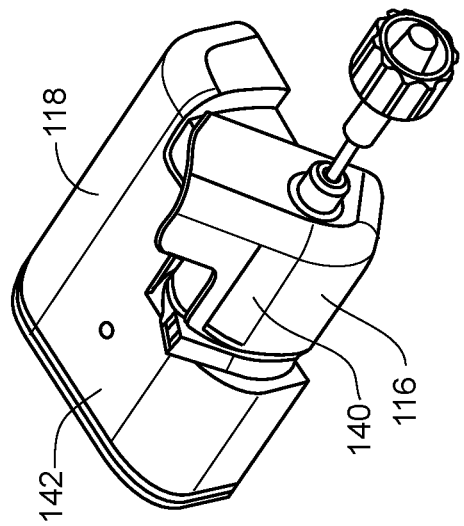
Figure 2C:
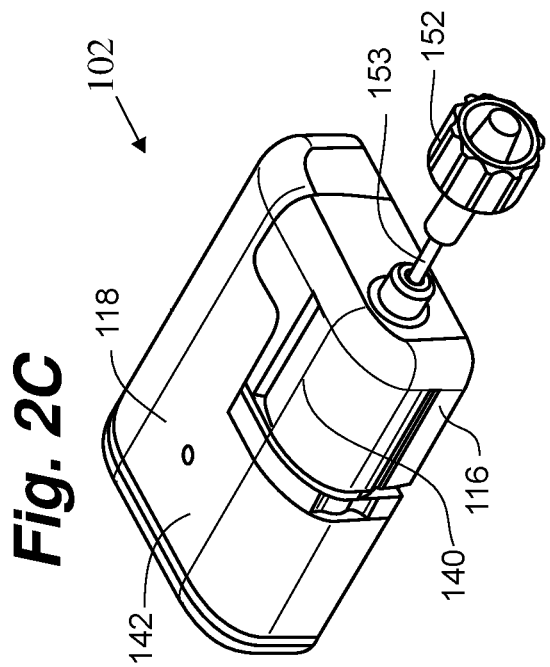
Figure 5A:
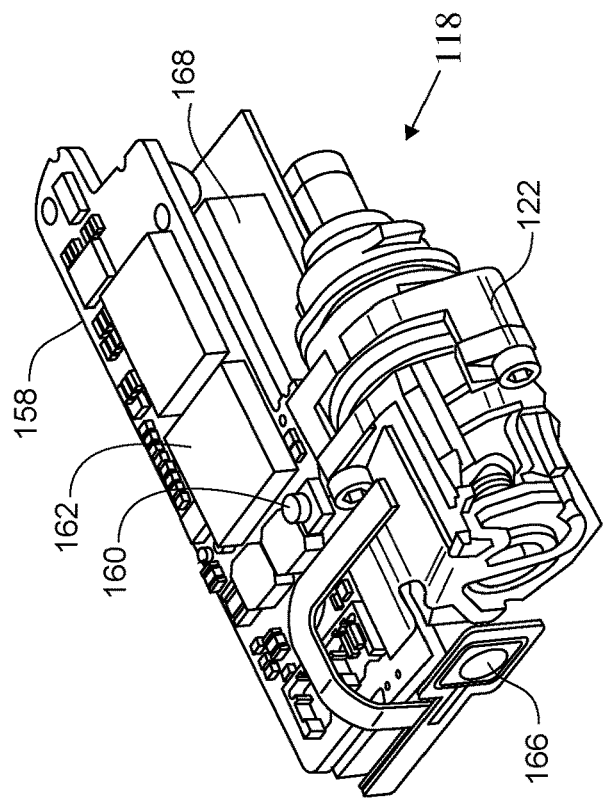

In some embodiments, and as shown in FIGS. 1C-1E and in FIGS. 2A-2C, cartridge 116 of pump 102 can attach to drive unit 118 with a rotational attachment. Recess 124 of cartridge 116 can be configured to initially attach to drive mechanism 122 of drive unit 118 such that an outer surface 140 of the cartridge 116 is offset from an outer surface 142 of the drive unit 118 at an angle of, e.g., about 90 degrees as shown in FIGS. 1C-1E (generally perpendicular). The cartridge 116 can then be rotated toward the drive unit 118 to align the outer surface 140 of the cartridge 116 generally parallel with the outer surface 142 of the drive unit 118 and secure the cartridge 116 on the drive unit 118. In one embodiment, the engagement of the cartridge 116 to the drive unit 118 made by this rotation can cause an audible clicking sound that provides an auditory indication to the user that the cartridge is properly attached. Such a feature can alternatively or additionally provide a tactile indication to the user that the cartridge is properly attached. Although described above as an about 90 degree rotation, it should be understood that a wide variety of rotational angles can be employed, such as the angle of approximately 60 degrees shown in FIGS. 2A-2D, or any angle between about 30 degrees and about 150 degrees. FIGS. 3A-3D depict further detail regarding such an attachment, which is further described in U.S. patent application Ser. No. 15/158,125 referenced above.

Also depicted in the embodiment of FIGS. 2A-2C is a short length of tubing 153 and a connector 152. Connector 152 is designed to attach to a corresponding connector of an infusion set that includes a length of tubing extending from the corresponding connector to an infusion site having an infusion site connector to deliver medicament to the infusion site. In some embodiments, connector 152 extending from cartridge 116 and the corresponding connector of the infusion set can be Luer Lock connections. Other infusion set configurations and attachments are described in U.S. Patent Publication No. 2014/0276423, which is hereby incorporated by reference in its entirety.

Figure 4A:
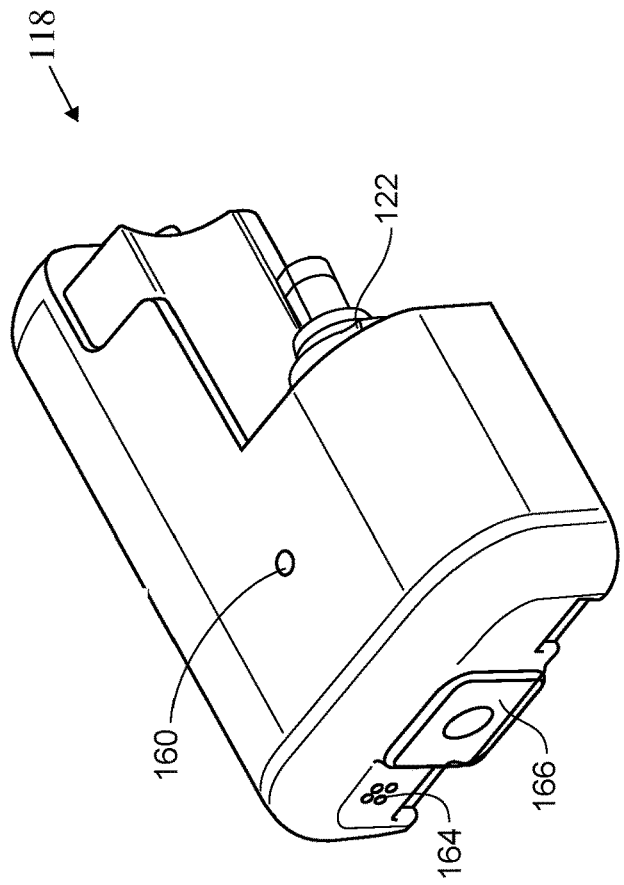
Figure 5C:
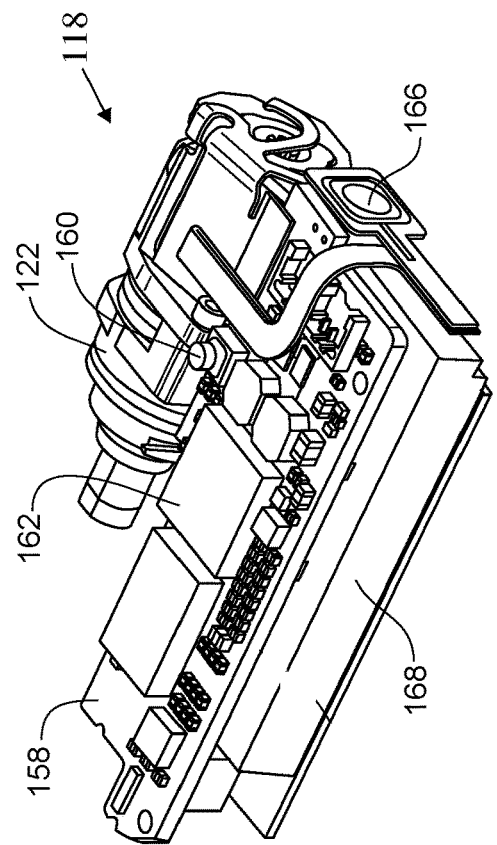
Figure 4C:
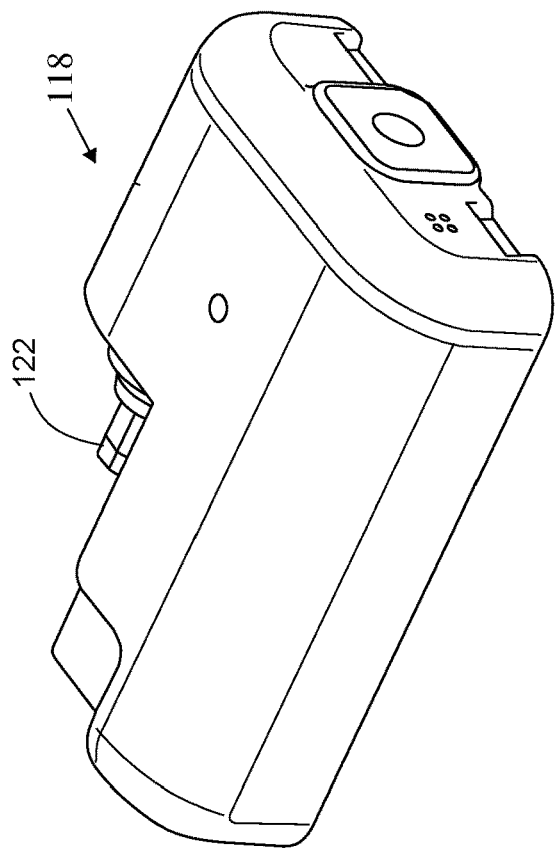

FIGS. 4A-4C and FIGS. 5A-5C, which mirror FIGS. 4A-4C except that the housing of the drive unit has been removed for sake of clarity, depict various views of a drive unit 118 for a patch pump system 100 according to an embodiment of the present invention. Drive mechanism 122 is contained within drive unit 118 and is configured to be attached to a cartridge 116 of the pump 102 as discussed above. Drive unit 118 can include an internal printed circuit board assembly (PCBA) 158 including an indicator light 160 used to provide visual feedback to the user regarding operation of the pump and an audio indicator 162, such as a speaker, that can be used to provide audible feedback to the user. A vent 164 can provide a dual function of being an outlet for the audible feedback emitted from the audio indicator 162 and venting pressure from within the device. A vibratory motor 172 can also be included and can provide vibratory feedback to the user. A function button 166 can be used to control operation of the device. Power can be provided to device by a battery 168, which, in some embodiments, can be inductively charged using an inductive charging coil 170.

FIGS. 6A-6C and 7A-7E depict a drive mechanism 122 that utilizes piezoelectricity to dispense medicament from a cartridge syringe in a pump system such as patch pump system, one example of which is patch pump system 100 including a patch pump 102 as described above, according to an embodiment of the present invention. In general, drive mechanism 122 includes a plurality of piezoelectric elements that when energized with a drive signal oscillate against a drive disk to induce rotational motion of the drive disk. The rotational motion of the drive disk is converted to linear motion of a pushrod that interfaces with the syringe in the cartridge to advance the syringe and dispense medicament.

Figure 6A:
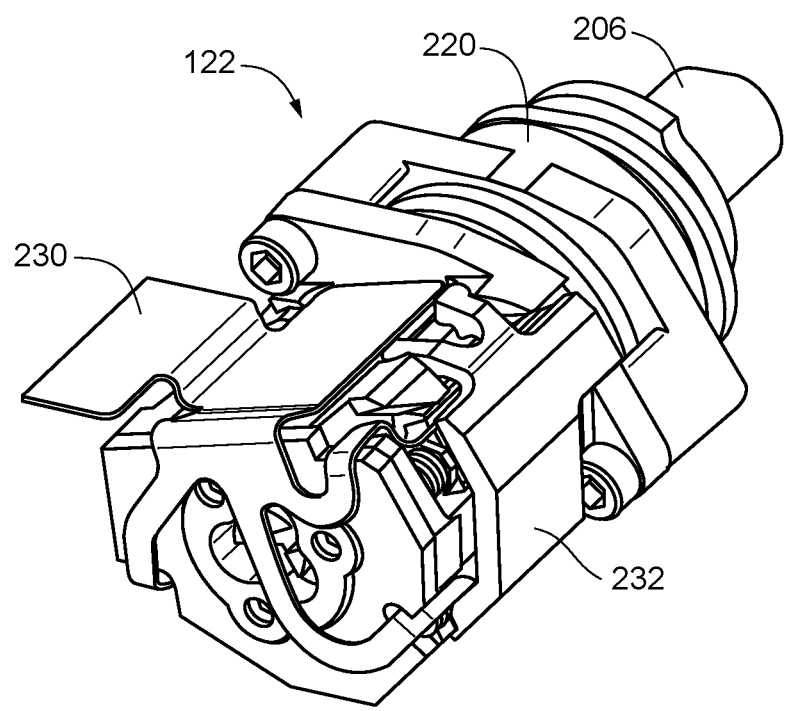
FIGS. 6A-6C depict perspective views of a drive mechanism for a patch pump according to an embodiment of the present invention.
Figure 6C:
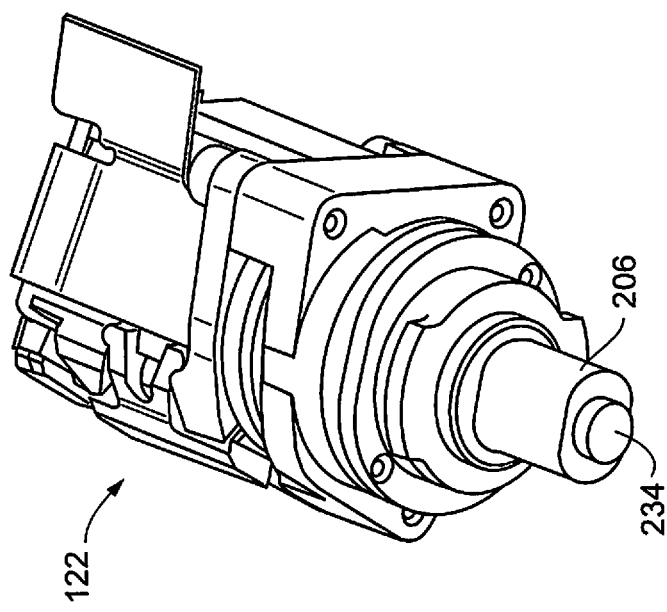
Figure 6B:
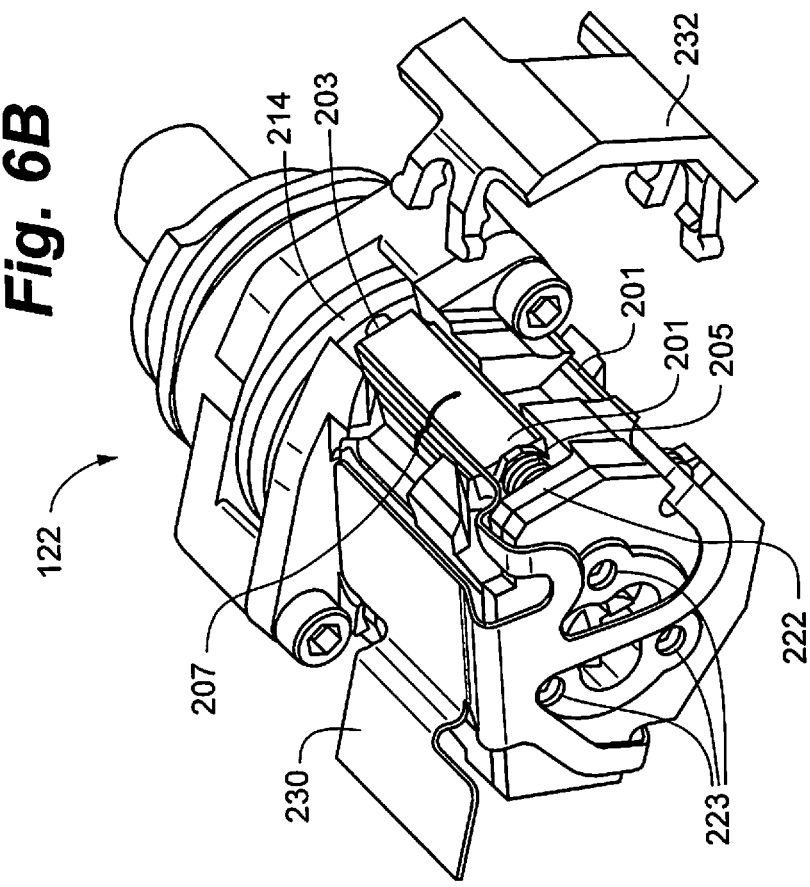
Figure 7A:
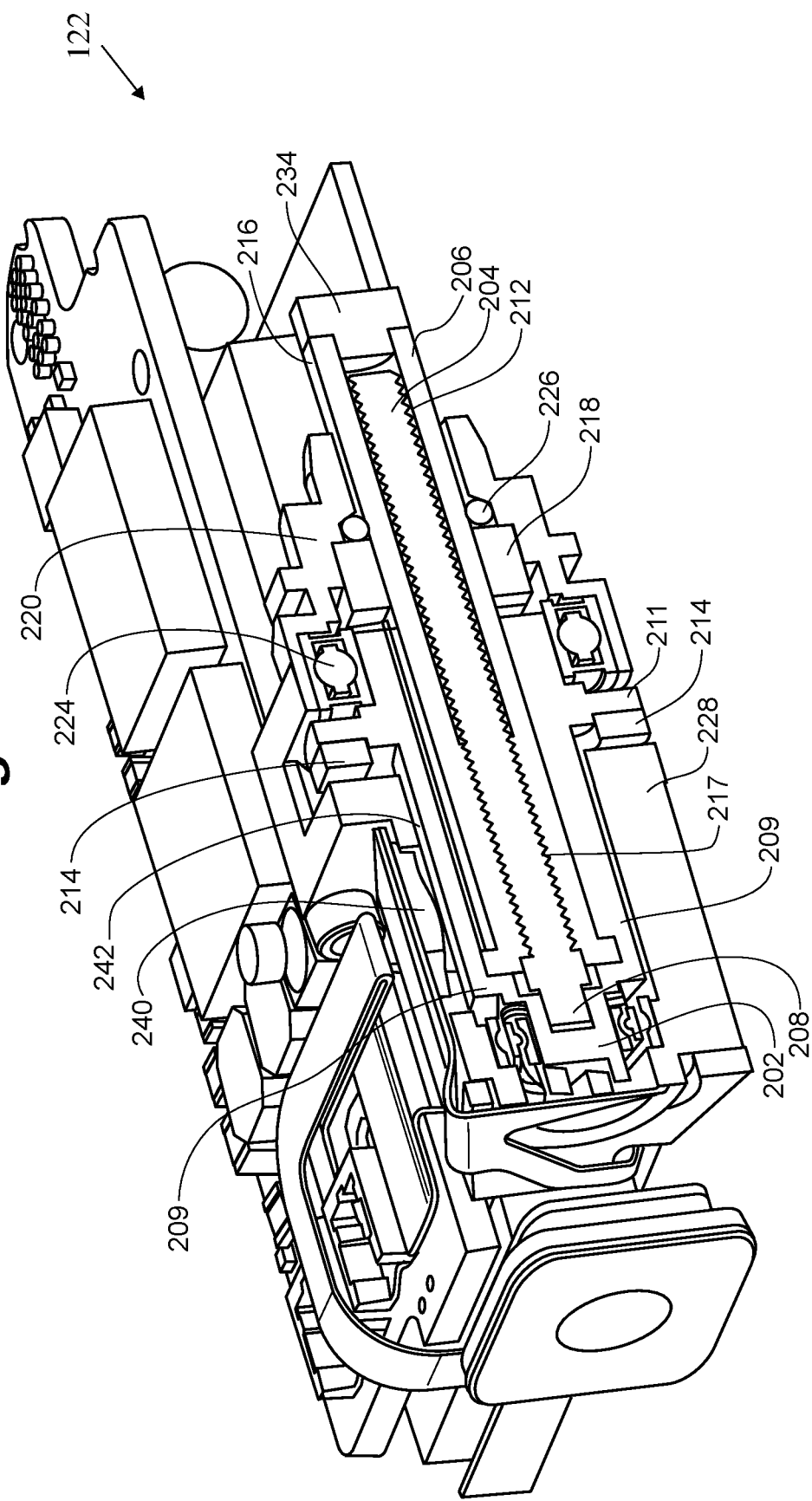
FIGS. 7A-7E depict various views of a drive mechanism for a patch pump according to an embodiment of the present invention.
Figure 7B:
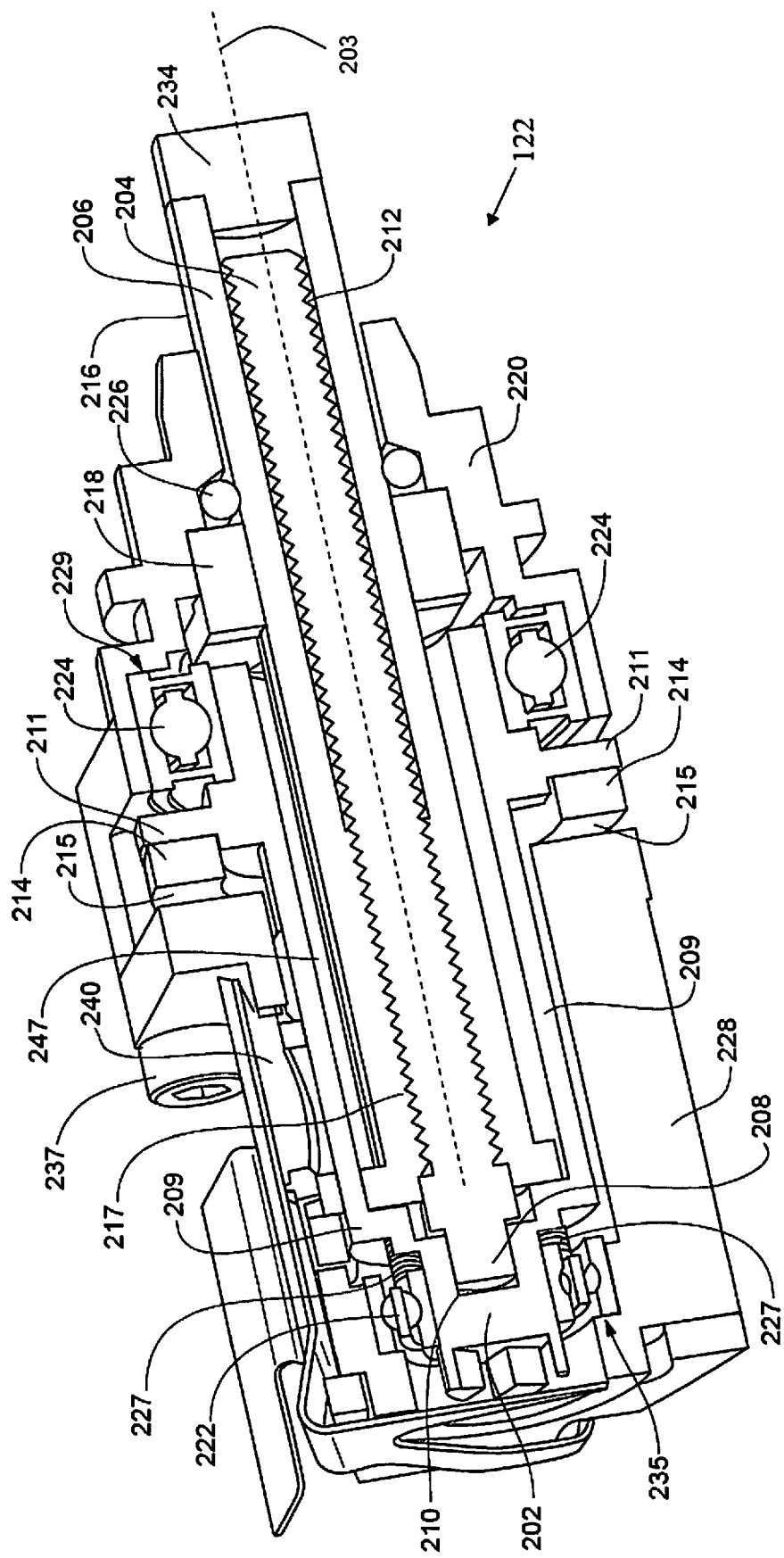
Figure 7C:
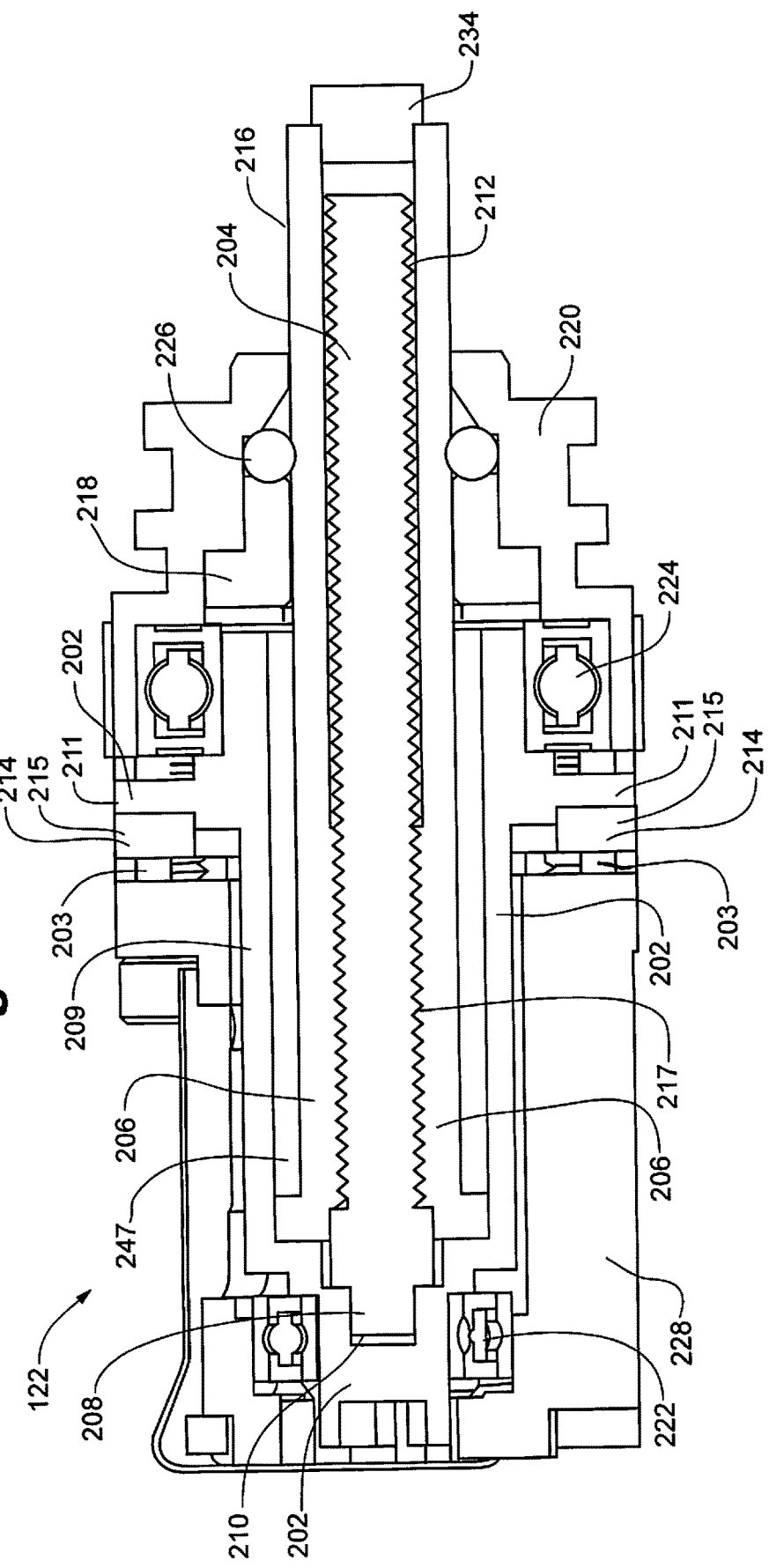
Figure 7D:
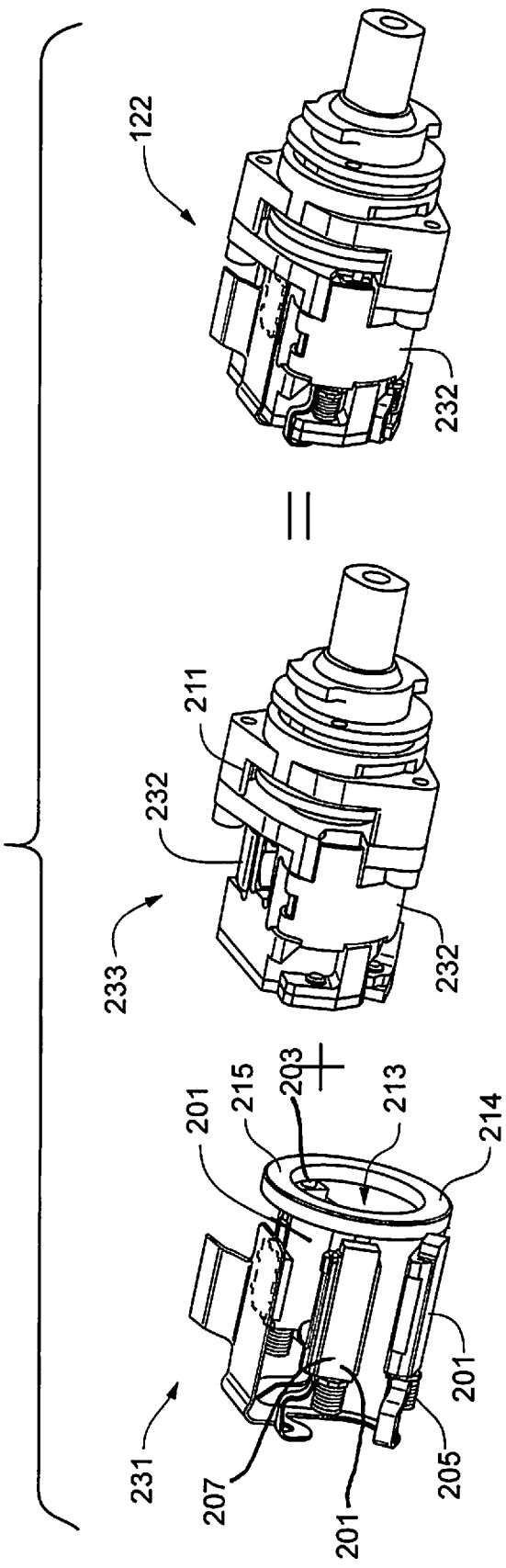
Figure 7E:
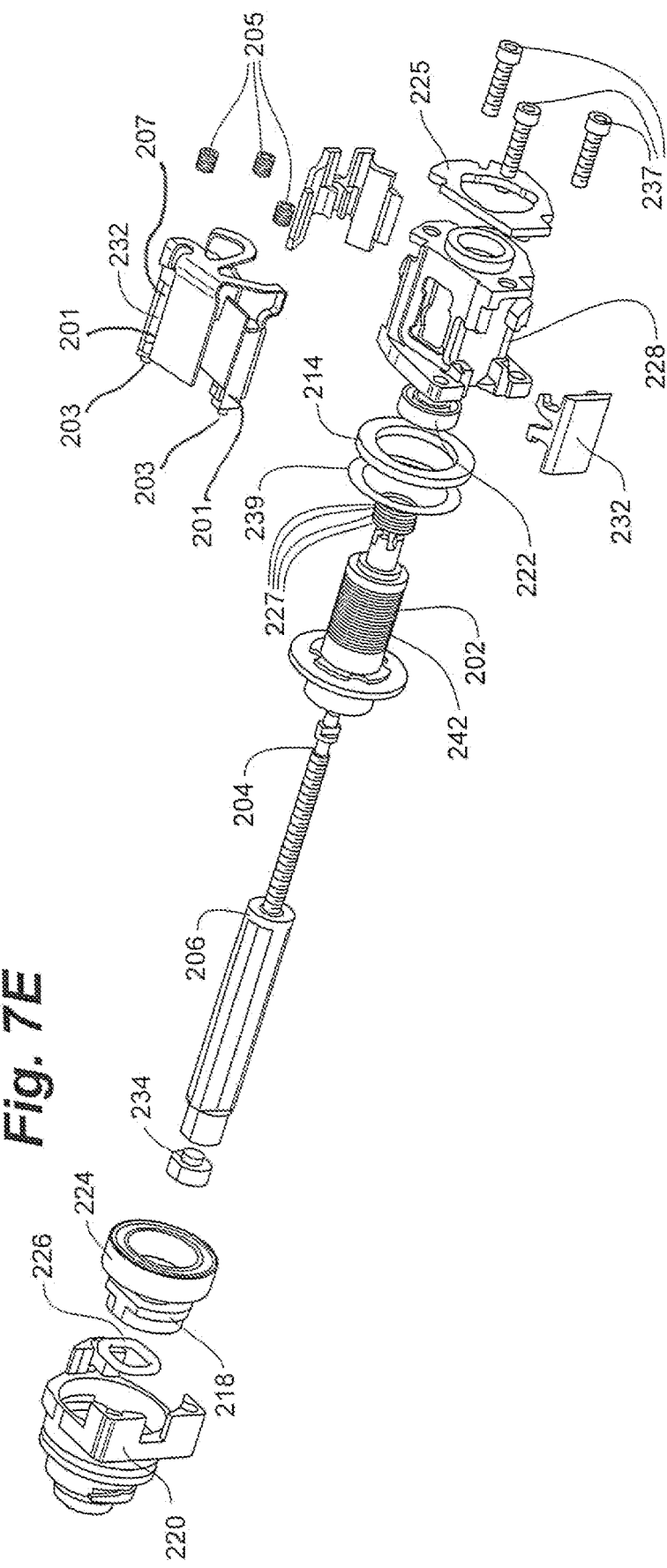

In the depicted embodiment, the piezoelectric elements that drive the system are three piezoelectric crystal motors 201 contained within the drive mechanism 122, although it should be understood that greater or fewer numbers of motors could be used. One type of piezoelectric motor that may be used in various embodiments of the present invention is the Edge Motor sold by Nanomotion Ltd. Of Yokneam, Israel, a Johnson Electric Company. Motors 201 can be arranged in separate housings 207 concentrically positioned around the drive mechanism 122 and each can include a drive tip 203 at one end that contacts the drive disk, such as ceramic drive disk 214, along a body portion 215 of the ceramic drive disk 214. Drive disk 214 can be configured, for example as shown in FIGS. 7A-7E, as an open ring. A coil spring 205 can be positioned at an opposite end of each motor 201 and be biased to ensure that the drive tips 203 of the motors 201 maintain contact with the ceramic drive disk 214 with the appropriate amount of force. In the depicted embodiment, the coil springs 205 can be retained by a spring retention end cap 225 and the bias can be provided to the coil springs 205 by a rear bearing 222, which can include a plurality of set screws 223, as shown in FIG. 6B, or a plurality of shim washers 227, as shown in FIGS. 7B and 7E. Set screws 223 or shim washers 227 can be used to adjust the extent of the preload provided to the coil springs 205 by the rear bearing 222. In the depicted embodiments, there are three set screws 223 or five shim washers 227. Alternatively, in place of set screws or shim washers providing the preload bias, a threaded cap, wave spring, or elastomeric spring (o-ring), or any combination thereof, could be employed. Drive mechanism 122 can further include one or more retention clips 232 that aid in retaining the piezoelectric drive components 231 on a base portion 233 of drive unit 118 (see FIGS. 7D and 7E). The depicted embodiment includes two such clips 232.

The primary elements of the motor assembly utilized to translate the rotational motion of the ceramic drive disk 214 induced by the motors 201 into linear motion include a drive tube 202, a lead screw 204 and a drive nut or pushrod 206. As can be most clearly seen in FIGS. 7A-7C, the ceramic drive disk 214 is coupled to the drive tube 202 with a body 209 of the drive tube 202 extending through an opening 213 in the ceramic drive disk 214 and the body 215 of the ceramic drive disk 214 abutting a flange 211 of the drive tube 202. This interconnection of the ceramic drive disk 214 and drive tube 202 causes rotation of the ceramic drive disk 214 to induce rotation of the drive tube 202. In one embodiment, the ceramic drive disk 214 and drive tube 202 are attached to each other with a pressure sensitive adhesive 239 combined with an epoxy (See FIG. 7E). Alternatively, these components can physically interlock with each other such as, for example, with a key feature, hex, square, splines, polygon shape, etc. A proximal end 208 of the lead screw 204 is received within and coupled to a recess 210 in the drive tube 202, such that rotation of the drive tube 202 also rotates the lead screw 204. An internally threaded portion 217 of the pushrod 206 is coupled with external threads 212 of the lead screw 204. The external perimeter 216 of the pushrod 206 can be non-circular and slidably mated with a guide bushing 218 coupled to and contained within a front housing 220 to prevent the push rod 206 from rotating. This in turn enables rotation of the lead screw 204 to effect linear motion of the push rod 206. The push rod 206 is therefore contained within and directly driven by the motor assembly. A drive tip 234 can be attached to a distal end of the pushrod 206.

Various other components can be included in drive mechanism 122. Screws 237 extend from rear housing 228 to front housing 220 to retain device components together. Rear bearing 222 and a front bearing 224 can interface with the drive tube 202. A front seal 226 is provided between the front bearing 224 and guide bushing 218 to seal the interior of the drive mechanism 122. An additional sliding seal 247 that slides along the push rod 206 as it is advanced from the drive mechanism 122 can be included to provide redundant seals that prevent water and other liquid and/or contaminants such as dust, etc. from leaking into the system. Drive mechanism 122 can also include a flexible printed circuit board 230 that controls operation of the unit. In some embodiments, all electrical connections for each of the motors 201 can be contained on this flexible circuit board 230.

In one embodiment, operation of the unit is accomplished by energizing the piezoelectric motors with an electrical drive signal to cause them to oscillate against the ceramic drive disk 214. This oscillation induces rotational motion of the ceramic drive disk 214. Rotational motion of the ceramic drive disk 214 causes the drive tube 202 and the lead screw 204 to rotate. The intermeshing threaded exterior portion 212 of the lead screw 204 and interior threaded portion 217 of the pushrod 206 along with the non-circular perimeter 216 of the pushrod 206 that is constrained from rotating by the guide bushing 218 cause this rotational motion to be converted into linear motion of the pushrod 206. When the drive mechanism 122 is attached to a cartridge containing medicament, such as cartridge 116, the linear motion of the pushrod 206 causes the drive tip 234 of the pushrod to advance a syringe in the cartridge to cause medicament to be dispensed from the cartridge. Motors can be driven in parallel such that if one of the motors were turned off or not receiving the electrical drive signal, the non-energized motor would act as a friction brake due to the spring loading of the motor against the ceramic drive disk. The other two motors would continue to operate such that the system could still be in use with a non-functioning motor, however, the torque output would be significantly reduced relative to three operating motors. In other embodiments, greater or fewer than three motors can be employed, such as, for example two motors, with the number of motors affecting the amount of torque provided.

In some embodiments, drive mechanism 122 can further include a force transducer used to determine if the mechanism is functioning properly when activated to dispense medicament. Referring to FIG. 7B, in some embodiments, a force transducer can be located between the front bearing 224 and the front housing 220, as indicated, for example, by location 229. In such embodiments, axial force on the lead screw 204 when the device is operated will be transferred through the drive tube 202 such that force on the transducer 229 will decrease under a drive load. In other embodiments, a force transducer can be disposed between the rear bearing 222 and the rear housing 228 as indicated, for example, by location 235 in FIG. 7B. In such embodiments, axial force on the lead screw 204 during operation will be transferred through the rear bearing 222 to the transducer such that the force on the transducer 235 will increase under a drive load. In either type of embodiment, the respective decrease or increase in force will indicate that the device is operating properly, whereas the lack of decrease or increase will indicate that the device is not operating properly, such as when there is an occlusion preventing medicament from being dispensed from the cartridge. One or more of transducer 229 and/or transducer 235 can therefore be used as a means for detecting occlusions in patch pump.

Figure 10C:
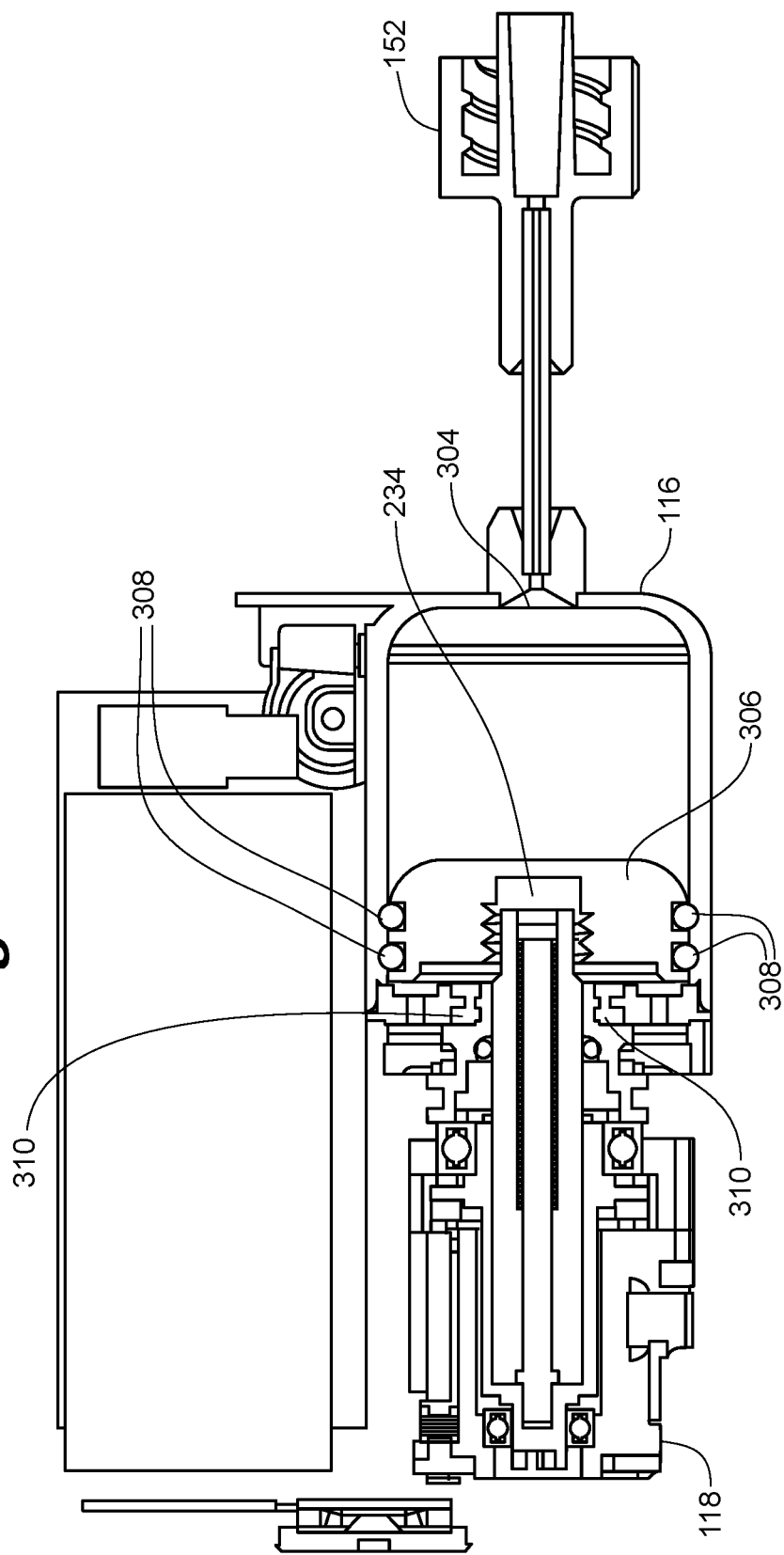

Further details regarding one embodiment of a cartridge 116 that can be used with patch pump 100 according to embodiments of the present invention are depicted in FIGS. 10A-10C. Cartridge 116 has a syringe type configuration with a reservoir 302 configured to be filled with a medicament such as insulin and a plunger 306. Drive tip 234 of drive mechanism 122 engages the plunger 306 to move the plunger 306 distally to force medicament out of an outlet port 304 and to the patient through connector 152, as discussed with respect to FIGS. 2A-2C. A pair of seals 308, such as o-rings, can provide a seal between the plunger 306 and an interior of the cartridge while still enabling the plunger 306 to slide within the cartridge. A water ingress seal 310 can be provided between the cartridge 116 and the drive unit 118 to prevent water from entering the pump at the connection these components. In one embodiment, cartridge is a single use cartridge intended to be disposed and replaced with a new cartridge after delivering the medicament in the reservoir. In another embodiment, the cartridge is intended to be refilled, via connector 152, and reused.

There are a number of benefits provided by a patch pump such as described herein utilizing a piezoelectric drive mechanism as opposed to use of a conventional electromagnetic motor as in current patch pumps. A piezoelectric drive unit can be made smaller than an electromagnetic motor of the same capability and typically has fewer moving parts because no gear reduction is needed to generate the force required to drive the syringe to dispense medicament from the cartridge. In addition, a piezoelectric motor is capable of effecting micron-sized increments of motion that in turn allow for precise and small movements of the syringe without the need for a gear reduction system. A piezoelectric motor also can afford greater safety when acting to dispense medicaments such as, e.g., insulin, because such a motor can automatically brake the drive system when turned off or deactivated. This in turn can prevent the unintended dispensing of medicament. This braking effect is due in part to the friction that exists between the piezoelectric drive tip(s) and the ceramic drive disk. Another safety concern for syringe drive systems related to unintended motor movement is addressed with the system of the present invention because the piezoelectric motors require a specific AC drive signal, such that a short circuit in the system to a DC voltage source could not result in unintended motor movement.

As discussed herein, the terms gear reduction and gear transmission are used to refer to a system of one or more gears or other components that decrease the speed generated by the motor of an infusion pump system to increase the torque on the lead screw or syringe that causes medicament to be dispensed. Such a gear reduction system can include one or more gears, such as, e.g., spur gears, worm gears and/or planetary gears. A common conversion ratio is 256:1, meaning that the system transmits torque on the lead screw that is 256 times the torque generated by the motor. Other common conversion ratios range from 64:1 to 256:1. As noted above, no gear reduction is required to generate the force required to drive the lead screw in embodiments of the present invention because the disclosed piezoelectric-based system is capable of providing large enough torque and small enough rotational step size to achieve desirable infusion pressures and dispense delivery volumes. As such, the rotational output generated by the motor as reflected by the torque of the rotating drive disk is directly converted into torque on the lead screw in a generally 1:1 ratio. In other words, the high torque generated by the piezoelectric motors is directly converted into the same amount of torque on the lead screw, so no torque increasing gear reduction system is needed.

Because no gear reduction or gear transmission system is needed in embodiments of the present invention, the pushrod utilized to drive the syringe can be contained within and connected directly to the motor assembly. This "hollow motor" that is capable of containing the drive element for the system enables a syringe-type pump as described herein to be provided in a smaller size than has heretofore been possible with prior art electromagnetic-based syringe pumps and other pumps that utilized gear reduction systems. In one embodiment, the drive unit of the patch pump can weighs about 22 grams. In other embodiments, the drive unit of the patch pump can weigh from about 17 grams to about 27 grams. The cartridge can have a capacity of about two milliliters of medicament. In such an embodiment, the patch pump can weigh about 30 grams when the cartridge is full and attached to the drive unit. In other embodiments, the cartridge can have a capacity of from about one milliliter to about three or more milliliters of medicament.

An additional feature that can be utilized by a drive mechanism according to embodiments of the present invention is an optical encoder system. Referring to FIG. 8A-8C, the device according to one embodiment can include an optical encoder integrated circuit 240 configured to monitor markings 242 radially around an outer perimeter surface 244 of the drive tube 202 (note that FIG. 8B depicts a drive mechanism embodiment with certain rear portions of the device removed and FIG. 8C depicts only drive tube 202, both for sake of clarity). The optical encoder integrated circuit 240 can include a reflective optical encoder with an integrated light source. The light source is positioned above the markings 242 on the drive tube 202, which can be a pre-defined series of reflective and non-reflective lines. By tracking the series of lines as the drive tube 202 is rotated, the integrated circuit monitors a rotational position of the drive tube 202.

In one embodiment, the optical encoder system can monitor three output channels that are indicated by the markings 242 on the drive tube 202. These can include, for example, an A channel, a B channel and an index channel. Monitoring of the A channel and the B channel can be used by the system to determine the rotational position, speed, and direction of rotation of the drive tube. Monitoring of the index channel can serve a number of purposes. For example, the index channel can be configured such that one index pulse is expected for a set number of A and B pulses. If the index channel pulse is not detected after the set number of A and B pulses, the encoder system is not operating properly, and one or more signals can be sent to a processor or other device to disable the drive system, send a warning or other message to a user, etc. Similarly, this configuration can be used to determine if the drive tube moved when the encoder system was not turned on. This configuration can further be used to determine if the A and B channels are operating as expected, because if so one index pulse should be received for each set number of A and B pulses as noted above. In the described optical encoder system, the markings 242 that are monitored are provided on a component of the system, drive tube 202, that otherwise serves an additional functional purpose (rotating the lead screw). As such, cost and complexity of the system are reduced by not requiring a separate, stand-alone part, such as a code wheel, for such monitoring. In addition, the electrical connections required for the encoder system can be provided on the same flexible circuit board 230 as the electrical connections for the motors 201, further reducing the cost and complexity of the system.

Figure 9:
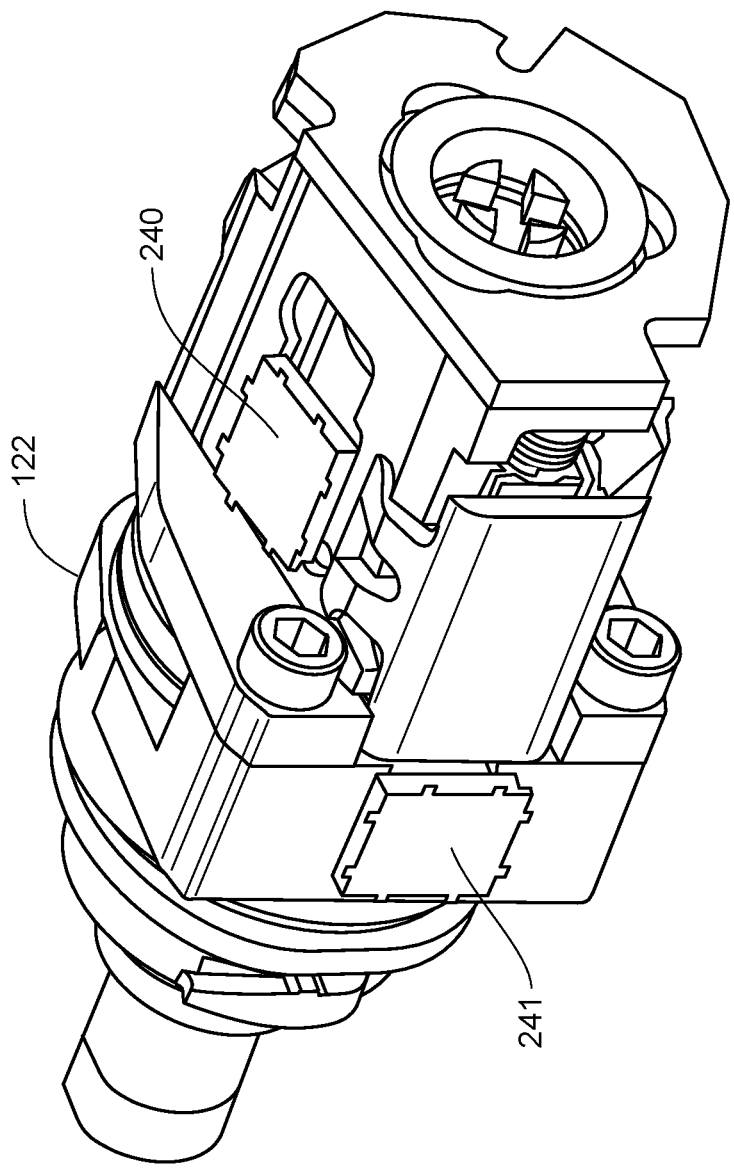
FIG. 9 depicts a perspective view of a drive mechanism for a patch pump according to an embodiment of the present invention.

Referring to FIG. 9, in one embodiment a patch pump can include a second encoder 241 in addition to encoder 240. The second encoder 241 can be positioned as shown in FIG. 9 to also monitor markings on the drive tube. In such an embodiment, the drive tube 202 may include a second set of optical markings for monitoring by the second encoder 241 in addition to the markings 242 discussed with respect to FIGS. 8A-8C. Utilization of a pair of encoders 240, 241 enables signal redundancy to prevent a single encoder fault from causing over delivery of medicament. Alternatively, instead of a second optical encoder the second encoder could be a magnetic encoder, Hall effect encoder, or other type of encoder known in the art.

Although primarily described herein as being employed in the context of a patch pump, it should be understood that the drive mechanism 122 described herein can be used with various other types of infusion pumps, such as, for example, the user-wearable infusion pumps described in the applications incorporated by reference herein.

Although the embodiments herein are specifically described with respect to the delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Also incorporated herein by reference in their entirety are commonly owned U.S. Pat. Nos. 8,287,495; 8,408,421 8,448,824; 8,573,027; 8,650,937; 8,986,523; 9,173,998; 9,180,242; 9,180,243; 9,238,100; 9,242,043; and 9,335,910 commonly owned U.S. Patent Publication Nos. 2009/0287180; 2012/0123230; 2013/0053816; 2013/0159456; 2013/0324928; 2013/0331790; 2013/0332874; 2014/0273042; 2014/0276419; 2014/0276420; 2014/0276423; 2014/0276531; 2014/0276537; 2014/0276553; 2014/0276556 2014/0276569; 2014/0276570; 2014/0276574; 2014/0378898; 2015/0073337; 2015/0072613; 2015/0182693; 2015/0182694; 2015/0182695; 2016/0030669; and 2016/0082188 and commonly owned U.S. patent application Ser. Nos. 14/707,851 and 15/158,125 and commonly owned U.S. Provisional Application Ser. Nos. 61/911,576; 61/920,902; 61/920,914; 61/920,940; 62/139,275; 62/207,748; 62/256,398; 62/272,255; 62/300,410; and 62/352,164.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A user-wearable infusion pump, comprising:
   a reservoir configured to include a medicament;
   an outlet port in fluid communication with the reservoir;
   a plunger disposed within the reservoir;
   a pushrod disposed adjacent the plunger;
   a threaded lead screw coupled to the pushrod;
   a drive tube connected to the threaded lead screw such that rotation of the drive tube causes rotation of the threaded lead screw to linearly advance the lead screw to move the pushrod against the plunger to drive medicament from the reservoir out of the outlet port, wherein the drive tube further includes a plurality of markings on an outer circumferential surface of the drive tube; and
   an optical encoder configured to monitor the plurality of markings on the outer circumferential surface of the drive tube to determine rotational positions of the drive tube.

2. The user-wearable infusion pump of claim 1, wherein the optical encoder comprises an integrated circuit and a light source.

3. The user-wearable infusion pump of claim 2, wherein the light source is positioned above the plurality of markings.

4. The user-wearable infusion pump of claim 1, wherein the plurality of markings are a pre-defined series of reflective and non-reflective lines.

5. The user-wearable infusion pump of claim 1, wherein the optical encoder is further configured to be used to determine a rotational speed and direction of the drive tube by monitoring the plurality of markings.

6. The user-wearable infusion pump of claim 1, wherein the optical encoder is configured to be used to monitor at least two output channels indicated by the plurality of markings on the drive tube including a first output channel and a second output channel.

7. The user-wearable infusion pump of claim 6, wherein monitoring of the first and second output channels is used to determine rotational position, speed and direction of the drive tube.

8. The user-wearable infusion pump of claim 7, wherein the optical encoder is further configured to be used to monitor a third output channel comprising an index channel such that one index pulse is expected for a set number of pulses from the first channel and the second channel.

9. The user-wearable infusion pump of claim 8, wherein monitoring of the index channel can determine if the optical encoder is not operating properly, if the drive tube rotated when the optical encoder was not activated and if the first and second channels are operating as expected.

10. The user-wearable infusion pump of claim 1, further comprising at least one piezoelectric motor configured to cause the drive tube to rotate when energized with an electrical signal.

11. A user-wearable infusion pump, comprising:
a cartridge including a reservoir configured to include a medicament, an outlet port in fluid communication with the reservoir and a plunger disposed within the reservoir;
a drive unit including a pushrod configured to drive the plunger, a threaded lead screw coupled to the pushrod and a drive tube connected to the threaded lead screw such that rotation of the drive tube causes rotation of the threaded lead screw to linearly advance the lead screw to move the pushrod against the plunger to drive medicament from the reservoir out of the outlet port, wherein the drive tube further includes a plurality of markings on an outer circumferential surface of the drive tube; and
an optical encoder configured to monitor the plurality of markings on the outer circumferential surface of the drive tube to determine rotational positions of the drive tube.

12. The user-wearable infusion pump of claim 11, wherein the optical encoder comprises an integrated circuit and a light source.

13. The user-wearable infusion pump of claim 12, wherein the light source is positioned above the plurality of markings.

14. The user-wearable infusion pump of claim 11, wherein the plurality of markings are a pre-defined series of reflective and non-reflective lines.

15. The user-wearable infusion pump of claim 11, wherein the optical encoder is further configured to be used to determine a rotational speed and direction of the drive tube by monitoring the plurality of markings.

16. The user-wearable infusion pump of claim 11, wherein the optical encoder is configured to be used to monitor at least two output channels indicated by the plurality of markings on the drive tube including a first output channel and a second output channel.

17. The user-wearable infusion pump of claim 16, wherein monitoring of the first and second output channels is used to determine rotational position, speed and direction of the drive tube.

18. The user-wearable infusion pump of claim 17, wherein the optical encoder is further configured to be used to modify a third output channel comprising an index channel such that one index pulse is expected for a set number of pulses from the first channel and the second channel.

19. The user-wearable infusion pump of claim 18, wherein monitoring of the index channel can determine if the optical encoder is not operating properly, if the drive tube rotated when the optical encoder was not activated and if the first and second channels are operating as expected.

20. The user-wearable infusion pump of claim 11, further comprising at least one piezoelectric motor configured to cause the drive tube to rotate when energized with an electrical signal.

* * * * *